(12) United States Patent
De la Fuente Klein et al.

(10) Patent No.: US 8,974,460 B2
(45) Date of Patent: *Mar. 10, 2015

(54) DEVICE FOR CONTROLLED ADJUSTMENT OF A SURGICAL POSITIONING UNIT

(75) Inventors: Matias De la Fuente Klein, Aachen (DE); Peter Belei, Aachen (DE); Klaus Radermacher, Stolberg (DE); Anthony Boyer, Echirolles (FR); Stéphane Lavallee, St Martin d'Uriage (FR)

(73) Assignee: Blue Ortho, Tronche (FR)

(*) Notice: Subject to any disclaimer, the term of this patent is extended or adjusted under 35 U.S.C. 154(b) by 172 days.

This patent is subject to a terminal disclaimer.

(21) Appl. No.: 13/124,956

(22) PCT Filed: Oct. 22, 2009

(86) PCT No.: PCT/EP2009/063930
§ 371 (c)(1),
(2), (4) Date: Apr. 19, 2011

(87) PCT Pub. No.: WO2010/046455
PCT Pub. Date: Apr. 29, 2010

(65) Prior Publication Data
US 2011/0218546 A1    Sep. 8, 2011

Related U.S. Application Data

(60) Provisional application No. 61/175,556, filed on May 5, 2009.

(30) Foreign Application Priority Data

Oct. 22, 2008   (DE) .................. 10 2008 052 680

(51) Int. Cl.
*A61B 17/56* (2006.01)
*A61B 17/88* (2006.01)
(Continued)

(52) U.S. Cl.
CPC .......... *A61B 17/8875* (2013.01); *A61B 17/155* (2013.01); *A61B 17/157* (2013.01);
(Continued)

(58) Field of Classification Search
USPC ................ 606/86 R–88, 90, 96–98, 57, 246
See application file for complete search history.

(56) References Cited

U.S. PATENT DOCUMENTS 4,669,359 A * 6/1987 Shiba ............................. 91/361
4,681,843 A   7/1987 Egerer et al.
(Continued)

FOREIGN PATENT DOCUMENTS

DE   100 29 737   5/2003
EP   0728446      8/1996
(Continued)

OTHER PUBLICATIONS

NN8810457, IBM Technical Disclosure Bulletin, Oct. 1988.*
(Continued)

*Primary Examiner* — Matthew Lawson
*Assistant Examiner* — Zade Coley
(74) *Attorney, Agent, or Firm* — Miles & Stockbridge PC

(57) ABSTRACT

The invention concerns a device for adjusting the position of a screw (13) that is able to move a part of a surgical instrument, said device (4) comprising: —a stem (41) comprising a tip (42) suited to the head (130) of the screw (13), —an actuated system (45) for driving said stem (41) in rotation, —communication means to communicate with a control unit (21), such that the control unit (21) transmits to the actuated system (45) the number of turns to apply to the stem (41) to reach the target position of the screw (13). The invention also concerns a surgical system for alignment of surgical guide means (14, 15), comprising: —a positioning unit comprising a fixed part (11) and a mobile part (12) supporting the surgical guide means (14, 15), the position of said mobile part (12) being adjustable with respect to the fixed part (11) by screws (13), —a referencing unit for detecting the position of the positioning unit with respect to a target position of the surgical guide means, —a control unit (21) for computing the target position of screws (13), —said device (4) for adjusting the positions of the screws (13).

18 Claims, 14 Drawing Sheets

(51) Int. Cl.
  *A61B 17/15* (2006.01)
  *A61B 17/17* (2006.01)
  *A61B 17/70* (2006.01)
  *A61B 17/86* (2006.01)
  *A61B 19/00* (2006.01)
  *A61B 17/00* (2006.01)

(52) U.S. Cl.
  CPC ........... *A61B17/175* (2013.01); *A61B 17/7076* (2013.01); *A61B 17/8615* (2013.01); *A61B 19/5244* (2013.01); *A61B 17/1757* (2013.01); *A61B 2017/00482* (2013.01); *A61B 2019/448* (2013.01); *A61B 2019/4857* (2013.01)
  USPC ...................................................... 606/86 R

(56) References Cited

U.S. PATENT DOCUMENTS

| | | | |
|---|---|---|---|
| 4,706,665 A | | 11/1987 | Gouda |
| 4,800,325 A | * | 1/1989 | Nakanishi ................... 318/661 |
| 4,813,312 A | * | 3/1989 | Wilhelm ........................ 81/467 |
| 4,973,331 A | * | 11/1990 | Pursley et al. .................. 606/54 |
| 5,010,263 A | * | 4/1991 | Murata ....................... 310/68 B |
| 5,014,794 A | * | 5/1991 | Hansson ....................... 173/181 |
| 5,121,558 A | * | 6/1992 | Caroe et al. ..................... 33/700 |
| 5,806,518 A | | 9/1998 | Mittelstadt |
| 6,172,824 B1 | | 1/2001 | Lehmann et al. |
| 6,554,837 B1 | | 4/2003 | Hauri et al. |
| 6,712,824 B2 | * | 3/2004 | Millard et al. ................. 606/87 |
| 7,126,628 B2 | * | 10/2006 | Liu ................................. 348/92 |
| 7,458,282 B1 | * | 12/2008 | Wuester et al. ........... 73/862.23 |
| RE43,328 E | * | 4/2012 | Foley et al. ................... 600/429 |
| 2002/0010465 A1 | | 1/2002 | Koo |
| 2002/0095083 A1 | * | 7/2002 | Cinquin et al. .............. 600/407 |
| 2003/0181800 A1 | * | 9/2003 | Bonutti ......................... 600/407 |
| 2003/0222979 A1 | * | 12/2003 | Liu ................................. 348/92 |
| 2004/0003683 A1 | * | 1/2004 | Rudduck ........................ 81/52 |
| 2004/0153083 A1 | * | 8/2004 | Nemec et al. .................. 606/86 |
| 2004/0243207 A1 | * | 12/2004 | Olson et al. .................. 607/116 |
| 2005/0149038 A1 | | 7/2005 | Haines et al. |
| 2005/0216032 A1 | * | 9/2005 | Hayden ......................... 606/130 |
| 2005/0234466 A1 | * | 10/2005 | Stallings ........................ 606/88 |
| 2005/0257599 A1 | * | 11/2005 | Kuo .............................. 73/12.01 |
| 2006/0032554 A1 | * | 2/2006 | Sprague et al. .............. 144/365 |
| 2006/0060092 A1 | * | 3/2006 | Wu ................................. 100/48 |
| 2006/0111726 A1 | | 5/2006 | Felt et al. |
| 2006/0122617 A1 | * | 6/2006 | Lavallee et al. ................ 606/87 |
| 2006/0217733 A1 | * | 9/2006 | Plassky et al. ................. 606/87 |
| 2006/0235290 A1 | | 10/2006 | Gabriel et al. |
| 2007/0055289 A1 | * | 3/2007 | Scouten et al. .............. 606/130 |
| 2007/0055389 A1 | | 3/2007 | Harwood |
| 2007/0085496 A1 | * | 4/2007 | Philipp et al. ................. 318/139 |
| 2007/0225704 A1 | * | 9/2007 | Ziran et al. .................... 606/57 |
| 2007/0233121 A1 | * | 10/2007 | Carson et al. .................. 606/72 |
| 2008/0140081 A1 | | 6/2008 | Heavener et al. |
| 2008/0149582 A1 | * | 6/2008 | Sluiter .......................... 212/179 |
| 2010/0286710 A1 | | 11/2010 | Boyer et al. |
| 2011/0004199 A1 | * | 1/2011 | Ross et al. ....................... 606/1 |

FOREIGN PATENT DOCUMENTS

| | | | |
|---|---|---|---|
| EP | 1 444 957 | | 8/2004 |
| EP | 1 574 170 | | 9/2005 |
| EP | 1 665 992 | | 6/2006 |
| EP | 1 669 033 | | 6/2006 |
| EP | 1 679 047 | | 7/2006 |
| JP | 2002134307 A | * 5/2002 | ............ H01C 10/00 |
| WO | 01/78015 | | 10/2001 |
| WO | 02/37935 | | 5/2002 |
| WO | 03/009768 | | 2/2003 |
| WO | WO 2006/100458 | | 9/2006 |
| WO | WO 2006/106419 | | 10/2006 |
| WO | 2009/105479 | | 8/2009 |

OTHER PUBLICATIONS

NN8810446, IBM Technical Disclosure Bulletin, Oct. 1988.*
Amiot et al.; "Comparative Results Between Conventional and Computer-Assisted Pedicle Screw Installation in the Thoracic, Lumbar, and Sacral Spine"; Spine; 2000; vol. 25; No. 5; pp. 606-614.
Hamadeh et al.; "Automated 3-Dimensional Computed Tomographic and Fluoroscopic Image Registration"; 1998; Computer Aided Surgery; Biomedical Paper; vol. 3; pp. 11-19.
Horn; "Closed-Form Solution of Absolute Orientation Using Unit Quaternions"; 1987; Journal of the Optical Society of America A; vol. 4; p. 629.
Merloz et al.; "Computer Assisted Spine Surgery"; 1998; Computer Aided Surgery; vol. 3; pp. 297-305.
International Preliminary Report on Patentability Based on International Application No. PCT/EP2009/063930 Issued Apr. 26, 2011.
Kosmopoulos et al; "Pedicle Screw Placement Accuracy"; A Meta-Analysis, Spine; 2007; 32(3): E111-20.
Grutzner et al.; "Klinische Studie Zur Registrierungsfreien 3D-Navigation Mit Dem Mobilen C-Bogen Siremobil Iso-C 3D, Electromedica"; 2003; 71(1):58-67.
Schaeren et al; Effektive In-Vivo-Strahlendosis Bei Bildwandlerkrontollierter Pedikelinstrumentation vs. CT-Basierter Navigation; Orthopade; Apr. 2002; 31(4):392-396.
Laine et al.; "Accuracy of Pedicle Screw Insertion With and Without Computer Assistance: A Randomised Controlled Clinical Study in 100 Consecutive Patients"; European Spine Journal; 2000; 9(3):235-240.
Sukovich et al; "Miniature Robotic Guidance for Pedicle Screw Placement in Posterior Spinal Fusion: Early Clinical Experience With the Spineassist"; International Journal of Medical Robotics and Computer Assisted Surgery; Jun. 2006; 2(2):114-22.
Wendl et al; "Iso -C3D-Gestutzte Navigerte Implantation Von Pedkiel-Schrauben an BWS Und LWS"; Unfallchirurg; Nov. 2003; 106(11):907-913.
Susil et al.; "A Single Image Registration Method for Ct Guided Interventions" MICCAI '99; Springer-Verlag Berlin Heidelberg (1999); LNCS 1679; pp. 798-808.
International Search Report based on PCT/EP2009/063930 mailed Feb. 8, 2010.

* cited by examiner

DEVICE FOR CONTROLLED ADJUSTMENT OF A SURGICAL POSITIONING UNIT

CROSS REFERENCE TO RELATED APPLICATIONS

This application is a §371 National Stage Application of PCT/EP2009/063930 filed Oct. 22, 2009, which claims priority to DE 10 2008 052 680.0 filed Oct. 22, 2008 and U.S. Provisional Application No 61/175,556 filed May 5, 2009.

FIELD OF THE INVENTION

The invention concerns an adjustment device for adjusting the position of a screw that is able to move a part of a surgical instrument, a surgical positioning unit supporting surgical guide means, such as drill guides and cutting planes, and a method for the adjustment of surgical guide means.

BACKGROUND OF THE INVENTION

During transpedicular instrumentation of vertebral column segments, the insertion of surgical implant close to sensible structures requires a very high degree of precision. For protection of nerves in proximity and blood vessels a high number of control X-ray images is acquired causing an increased irradiation. Despite multiplanar X-ray control there is a relatively high rate of misplaced implants caused by the difficulty of deducing 3D information from the acquired images and by the freehand drilling. According to a meta analysis by Kosmospoulos and Schizas[1] taking into account 130 ex- and in-vivo studies regarding accuracy of pedicle screw placements there is a variance of 0%-72% (median 10%) of implantation failure rate using conventional technique.

For better control of implantation and in order to avoid perforations, a multitude of computer assisted navigation and robotic systems especially in the domain of spine surgery have been developed and commercialized by research laboratories and by the industry. For spine surgery, especially in minimally invasive procedures, most computer assisted surgery systems use medical images for input patient data. From a methodological point of view these systems can be classified by the image modality (preoperative Computer Tomography (CT), intraoperative 2D, respectively 3D, fluoroscopy) and by the registration method of transfer of the planning into the operating site (navigated or robotically). Depending on the underlying principle, the surgical workflow as well as the advantages and disadvantages resulting from the respective boundary conditions change with respect to the conventional technique.

Generally speaking, computer assisted systems could prove in the framework of clinical studies, that the failure implantation rate of pedicle screws can be reduced significantly to 0%-28% (Median 5%) with respect to conventional approach[1]. Additionally, Grützner et al.[2] demonstrated in the framework of a clinical study, that by use of fluoroscopic navigation systems (2D or 3D) the irradiation dose could be reduced by up to 40% respectively 70%. Especially the Operating Room staff took advantage from this reduction besides the patient, the former being exposed to such irradiation on a daily basis during such interventions.

This positive tendency is not valid for CT based systems though, for which the overall irradiation balance for the patient is disadvantageous with respect to the conventional approach because of the navigation data set that needs to be acquired additionally to the diagnosis CT data set[3]. Additionally there are supplemental costs for the CT data such that a CT based planning is only justifiable in the case where the structures to be treated show large deformations.

The necessary detail accuracy of the data sets is with few concessions also provided with intra operative 3D imaging or 3D Fluoroscopy. These systems (e.g. Siemens Arcadis Orbic) allow the navigation within multiplanar reconstructions but with reduced quality and especially with a reduced scan volume (approximatively 12 cm×12 cm×12 cm) with respect to pre operative CT data sets. A major advantage of the intraoperative 3D imaging however is, that the datasets are acquired intra operatively just before the implantation and that the registration can be done automatically. Thanks to this, the probability of anatomic alteration (e.g in the case of traumatological interventions) between the preoperative CT scan and the Operating Room as well as registration errors can be minimized. This is also potentially reflected when comparing the position failure rates of such systems (4%-9% CT based[4]-[7], under 1% 3D fluoroscopy[8]-[9]).

There are several advantages and disadvantages of the CT based and the 2D and 3D fluoroscopic navigation systems that are being discussed controversial in the literature. In more detail these issues are:
- Operating Room time compared to the conventional approach
- The invasiveness necessary for the intervention (size/type of incision, attachment of reference basis to the bone, etc.)
- Problems with the clinical and surgical workflow being modified in a different way
- Purchase cost and additional cost per intervention An important limiting factor of navigation based systems is the necessary tracking system (mostly optical tracking) by which the registration (alignment of the planning data with the patient anatomy) as well as the positioning and alignment of the implantation instruments is performed. On the one hand the intra operative flexibility is greatly reduced by the "line of sight" problem and the limited work space, on the other hand the achievable accuracy is limited for example because of markers being soiled by blood or the temperature sensibility of the sensor system. Furthermore there is the problem of free hand positioning of the instruments (drills, drill guides, cutting jigs) which causes the results being heavily dependent on the dexterity of the surgeon besides exact planning. There is no controversy that the expenses for navigation bases systems are significant when compared with the conventional approach. The necessary purchase of a tracking system (costs between 10000 € and 40000 €) is in the centre of focus here. There are additional costs for the different instruments (interfaces for the trackers on the instruments and guides, calibration tools, etc.) that are customized to the respective tracking based navigation system and for the costs for single use items necessary for each surgery (i.e. 500 €-1000 €).

A system being used for spine surgery in a clinical setting that does not require a tracking system neither for registration (automatic image based registration) nor for instrument alignment, is the semi active robotic assistance system SpineAssist® (Mazor Surgical Technologies, Caesarea, Israel)[10], also disclosed in WO 03/1009768. The system is attached to a reference basis that itself is attached dorsally to several segments of the vertebral column. This allows a robotically alignment of a drill guide in the direction of pedicle screw placement. After planning controlled alignment the robot is being switched off and the surgeon performs the drilling through the positioned drill guide. The system is based on pre operative CT data sets with the known advantages and disadvantages (except for the problems with registration). The alignment or so called registration between planning CT data set and the patient anatomy is carried out in a pure image based way by using biplanar fluoroscopic data sets (so-called "fluoromerge")[11] and calibration fiducials being integrated in the reference basis.

The Robodoc (see U.S. Pat. No. 5,806,518) is another robotic system that is used for surgical applications for hip and knee. Despite the advantages which result from the different functional principles described above with respect to tracking based free hand navigation one can summarizes the limitations of the system on the basis of the problems that are discussed generally in conjunction with robotic assisted surgery:

- Purchase costs (e.g. SpineAssist® approx. 120.000 €) plus additional costs per case.
- Safety related methodological efforts (e.g. redundant safety architecture), since active components are in touch with the patient.
- The operative and technological effort for maintaining sterility of the semi active robotic system (cable based system with six motor-encoder units).
- The application specific design (work space) of the robotic system comprising a specific kinematics with therefore designed electronics and drive unit which do not allow a universal application for different medical problems.

Furthermore there are different approaches originating in stereotactic neurosurgery. These systems allow the adjustment of a trajectory (e.g. to target a certain area in the brain) based on a 3D image data set (e.g. CT data set). The coordinate system of the stereotaxy frame is aligned with the planning image data set either by a direct unambiguous link to the reference frame of the CT-gantry, or by taking advantage of the visibility of certain parts of the stereotactic frame in the image data set. For a patent on this topic see for example U.S. Pat. No. 4,706,665, which describes a purely passive positioning system. Some axis of the articulated stereotactic frames can be driven electrically such that it becomes similar to a robotic system (see US 2007/0055389). The alignment of the stereotactic frame (respectively of the robot) can also be performed with positioning sensor technology as described in EP 0 728 446. WO 01/78015 and especially WO 02/37935 describes a system, where based on multiplanar X-ray images a planning for an osteotomy (bone cut) or respectively an osteosynthesis (alignment of two bone fragments) is generated with computer assistance and then realised with a mechanical device. More precisely the computer system calculates the necessary adjustment parameters for realising the plan, which is then adjusted accordingly by the surgeon. But those systems require robotics device to make it fast and accurate or they require manual adjustment of several screws which is slow and prone to human errors.

In those applications where patient images are used as input data, one objective of the invention is to provide a solution that does not require a navigation system or a robotics system but that is fast and easy to adjust accurately guides and instruments.

For applications outside of spine surgery, it is possible to assist the surgeon by a computer-assisted surgery system without using medical images. This refers to navigation systems. In those cases, using a navigation system with an optical or magnetic tracking system makes sense since it generates 3D data instead of medical images. Such data are used for optimal positioning of instruments. In navigation systems, trackers are attached to patient anatomical structures such as bone for example, but also to instruments such as cutting and drilling guides. However, the precise adjustment of cutting guides or drilling guides with navigation systems is usually done manually, using the navigation system as a visual control, or using adjustment guides with screws that are time consuming and cumbersome, and they may require additional fixations.

Many devices used in conjunction with navigation systems use screws to adjust and finely tune the position of a surgical instrument. For instance, in U.S. Pat. No. 6,712,824, Millar uses a mechanism with three screws to adjust a cutting plane guide for knee surgery, but the screws must be adjusted manually which takes time. Similar principles can be found in EP 1 444 957 by Cusick, or US 2006/0235290 by Gabriel. Moreover the mechanical architecture is serial and it does not lock automatically to a given position when the screws are not turned, it is therefore necessary to use additional pins in the bone to fix the guide.

More complex architectures are using more than three screws in order to adjust cutting blocks. For instance, in EP 1 669 033, Lavallee uses a navigation system to adjust the position of several screws of a femoral cutting block but this process is not easy and it takes a long time.

The tracking technology of navigation systems can take multiple forms. It includes, but is not limited to optical active technology, with active infrared Light Emitting Diodes (LEDs) on trackers, optical passive technology (with passive retro-reflective markers on trackers), mechanical passive arms with encoders, accelerometers and gyrometers, or magnetic technology. Those tracking technologies are known as prior art of navigation systems for surgery. In this type of applications which does not use medical images, it is therefore necessary to propose adjustments devices and methods to make fast, easy and precise positioning of surgical instruments using a navigation system.

Referring to FIG. 1, the instrument 1 is any surgical instrument that has the following characteristics:

[A] The instrument 1 has a tracker 10 attached thereon so that it is tracked by the navigation system 2. The navigation system 2 comprises a camera 20 and a control unit 21 such as a computer with a screen.
[B] The instrument 1 is rigidly fixed to a solid 3 that is also tracked by the navigation system 2.
[C] The instrument has a fixed part 11 which is fixed to the solid 3 and a mobile part 12 which is mobile with respect to the fixed part 11.
[D] The position of the fixed part 11 with respect to the mobile part 12 can be adjusted by screws 13. The number of screws is independent of the invention.

A tracker 30 is attached to the bone 3 or directly to the fixed part 11 of the instrument. It is used as a reference for collecting data points and surfaces with the navigation system. The target of cutting plane position is defined in a coordinate system attached to tracker 30.

A screwdriver 7 is used to adjust the instrument position with respect to the solid 3 in a target position. The target position of the instrument is supposed to be selected by the surgeon or set to default values with respect to anatomical landmarks digitized with the navigation system. The target position is represented by a geometric relationship M0 between the fixed part 11 of the instrument and its mobile part 12. By trivial calibration, the target position can be represented equivalently to a geometric relationship M1 between a tracker attached to the mobile part and a tracker attached to the fixed part or to the solid.

The problem is for the user to move several screws 13 independently to move the mobile part 12 until the geometric relationship between the mobile part tracker 10 and the solid tracker 30 matches M1 within a very low tolerance limit such as for instance 0.5 mm and 0.2°.

The manual adjustment of individual screws 13 takes a long time and it is difficult to converge towards a solution.

To help this process, for any initial position of the screws 13 and mobile part 12, the control unit 21 of the navigation system 2 can calculate the necessary screw differential adjustments DSi, for each screw 13i (where i is from 1 to N and N is the number of screws), which is necessary to bring the mobile part 12 to the target position. This is an easy calculation that only requires knowing the geometry of the screw placements with respect to the mobile and fixed parts and that is specific to each geometry. In a first step, the display of the navigation system can simply show the adjustments necessary DSi on each screw to the user such that the user follows the indications on the screen. While the screws 13 are manually adjusted, the values DSi are recalculated in real-time by the navigation system and the user can adjust the various screws accordingly.

However, this process remains long and complicated.

The present invention thus aims at providing an adjustment process that is short and simple in order to save intraoperative time and reduce the risk of failure, and an adjustment device suited for such a process.

SUMMARY OF INVENTION

This is achieved by a device for adjusting the position of a screw that is able to move a part of a surgical instrument, said device comprising:

a stem comprising a tip suited to the head of the screw, a actuated system for driving said stem in rotation, characterised in that it comprises communication means to communicate with a control unit, such that the control unit transmits to the actuated system the number of turns to apply to the stem to reach the target position of the screw.

The control unit is included in a navigation system or is connected to a medical imaging system.

Advantageously, the device comprises detection means for identifying which screw the tip of the device is in contact with, wherein the communication means of the device are able to transmit said identification information to the control unit.

According to a first embodiment of the invention, said detection means comprise a sliding stem able to slide inside the stem and a position sensor adapted to measure the displacement of the sliding stem with respect to the tip of the device.

According to a second embodiment, said detection means comprise electrical connectors arranged at the tip of the device and an ohmmeter.

According to a third embodiment, the detection means comprise a "Hall effect" sensor arranged in the tip of the device.

According to a fourth embodiment, said detection means comprise an optical sensor, a first optical fiber and a second optical fiber, the first and second optical fibers being arranged inside the stem so as to respectively light the cavity of the screw head and bring the reflected light to said optical sensor.

According to a fifth embodiment, said detection means comprises a tracker rigidly attached to the device.

Another object of the invention is a surgical system for alignment of surgical guide means with respect to a solid, said system comprising:

a positioning unit comprising a fixed part that is fixed with respect to the solid and a mobile part supporting the surgical guide means, the position of said mobile part being adjustable with respect to the fixed part by screws, a referencing unit for detecting the position of the positioning unit with respect to a target position of the surgical guide means, a control unit for computing the target position of screws, said system being characterised in that it comprises a device as described above for adjusting the positions of the screws.

The surgical guide means are generally drill guides or cutting blocks.

In one embodiment of the invention, the control unit is connected to an imaging system and the referencing unit comprises calibration markers that are detectable by the imaging system.

The referencing unit can be removably attached to an attachment unit rigidly fixed to the solid.

In another embodiment, the control unit is included in a navigation system and the referencing unit comprises a first reference element attached to the solid or to the fixed part of the positioning unit, that generates a first three-dimensional reference tracker, which is independently registered in the navigation system and a second reference element applied to the mobile part of the positioning unit that needs to be adjusted, that generates a second three-dimensional reference tracker, which is independently registered in the navigation system.

The position of the mobile part of the positioning unit is adjusted to a target defined by use of the navigation system, and the control unit determines the number of turns of the screws necessary to reach the target.

Advantageously, the system comprises means for indicating to the user which screw must be turned and how many turns must be applied to each screw to reach the target The system may also comprise a ruler on the positioning unit and/or on the adjustment device to adjust each screw.

In one preferred application of the invention, the system comprises an attachment unit for attachment to the spine of a patient, a referencing unit attached to the attachment unit and a positioning unit attached to the attachment unit and/or to the referencing unit, the positioning unit comprising four screws for adjusting the position and/or orientation of a drill guide.

In another preferred application of the invention, the system comprises an attachment unit for attachment to the femoral head of a patient, a referencing unit attached to the attachment unit and a positioning unit attached to the attachment unit and/or to the referencing unit, the positioning unit comprising four screws for adjusting the position and/or orientation of a drill guide.

In application of the invention to knee surgery, the positioning unit comprises a fixed part for attachment to the tibia or to the femur of a patient, a mobile part supporting a cutting plane and three screws for adjusting the position of the cutting plane with respect to the fixed part.

In another advantageous embodiment of the invention, the positioning unit is a spacer comprising two parallel plates and a screw for adjusting the distance between the plates.

The invention relates generally to surgical systems for alignment of surgical guides or instruments with respect to a well defined target (e.g. a planned cutting plane or a planned drilling bore in an object such as a bone).

Such surgical systems comprise:

a positioning unit, comprising a fixed part which is fixed with respect to the operated structure or object such as a bone, a mobile part supporting the surgical guide; the position of the mobile part with respect to the fixed part can be adjusted by screws.

a referencing unit, which function is to allow the determination of the position of the positioning unit with respect to the target; depending on the method involved, the referencing unit can comprise calibration markers that can be detected by an imaging system, or, when a navigation system is used, the referencing unit comprises trackers attached to the fixed part (or directly to the object) and to the mobile part.

An adjustment device that will be described in detail below allows an automated adjustment of the screws to the target position.

The adjustment device is driven by a control unit that is linked (wired or wireless) to the imaging system or to the navigation system, the control unit being able, taking into account the position of the positioning unit and of the target, to compute the number of turns to apply to each screw to reach the target.

In some cases, the fixed part of the positioning unit can be fixed directly to the object, e.g. by pins, or indirectly, the fixed part being thus fixed to an attachment unit which is itself rigidly fixed to the object.

More generally, the adjustment device is adapted for adjusting the position of any screw that is able to move a part of a surgical instrument.

Not only fixed positions (poses) count for a fixed spatial relationship, but all determinable or known relationships, from which the poses of the positioning unit and the referencing unit are determinable.

A positioning unit of the herein mentioned type is used for the spatial positioning (adjustment) of surgical guiding means. The referencing unit is used for determining the location of the positioning unit by means of 2D or 3D image data. The fixed spatial relationship between the referencing unit and the positioning unit can be discontinued temporarily. This can be used in particular for cleaning or adjustment of the positioning unit. Furthermore the temporary disconnection can have the advantage that the positioning unit is not attached to the patient in order to avoid having cumbersome components within proximity of the patient when using the positioning unit. For performing the surgical act (e.g. drilling in the spine) the spatial relationship is established again.

Using calibration markers included in a referencing unit, the position of the referencing unit with respect to images (or accordingly the orientation or accordingly the pose, whereas these analogies are valid for the remainder) can be determined. Several methods are known to calibrate the geometry of an imaging device and correct distortion of images at the same time.

For instance, in [11], calibration markers of a specific referencing unit are automatically detected by a computer that digitizes fluoroscopic 2D images and the known spatial arrangement of the individual markers makes it possible to compute a perspective matrix between coordinates of points in a coordinate system attached to the image and coordinates of points in a coordinate system attached to the referencing unit. In the case of 3D fluoroscopic images, standard point to point registration techniques can be used to match the markers detected in images with a known model of the spatial arrangement of those markers[12]. Hereby the calibration markers can have various types or shapes or arrangements, such as spheres, crosses, or Z-shaped structures like in standard stereotactic frames or registration features[13] for example. Based on these shapes and structures, an unambiguous determination of the position of the referencing unit can be carried out.

In a preferred embodiment the referencing unit is fixed to the fixed part of the positioning unit, and the position of the positioning unit is determined with respect to the medical images on which the target is defined.

For instance, in the case of 2D fluoroscopic images, the referencing unit contains at least 5 markers (usually 10 or 20) whose accurate positions are known by manufacturing in the coordinate system of the fixed part of the positioning unit to which it is attached in a reproducible manner. Standard x-ray image calibration techniques based on perspective matrices are used to register the image coordinate system with a coordinate system attached to the fixed part of the positioning unit. If necessary, an image distortion correction is performed at the same time by using the marker geometry as a reference or by using a secondary set of calibration markers arranged in a plane roughly parallel to the image plane. Those methods are well described in the literature. With at least 2D fluoroscopic x-ray images, it is possible to define a 3D surgical tool position or trajectory. The instance of a linear trajectory is taken. If the user defines a target trajectory on those x-ray images using a computer and a user interface, the target trajectory is therefore reconstructed in 3D in the coordinate system of the fixed part of the positioning unit. The mobile part position derives from the fixed part by the lengths of the screws. The kinematic model of the positioning device makes it possible to compute the position of the surgical guide from a series of screw length values. It is therefore necessary to invert the kinematic model to calculate the value of each screw such that the surgical guide will coincide with the target. Inverting a kinematic model is usually performed by using simple geometric rules for a parallel architecture and it depends on each specific mechanical design. This uses standard techniques developed for robotic control.

Hereby a defined adjustment of the mobile part of the positioning unit can be realised, which can be in particular based on a dataset defined in the computer.

By the fact that the positioning unit does not contain any active electrical components, electrical components cannot constitute a risk directly at the patient. Active electrical components comprise all components with an electric current flowing through them. Contrary to active components, passive components can be present with no risk, they are less cumbersome device, and they are less expensive.

In one embodiment of the invention, the positioning unit can have surgical guide means which comprise in particular drill guides or cutting jigs in such an advantageous way that the surgical guiding means can be moved or positioned in a defined way by the positioning unit using a plurality of screws.

In another embodiment of the invention, the surgical positioning unit can include an attachment unit, which allows to be attached to the anatomy. Hereby the positioning unit can be attached or detached to/from the attachment unit in an advantageous way. This can increase the versatility of the system. Furthermore it can be advantageous, that the adjustment is not done on the patient directly.

In a preferred embodiment of the invention, the referencing unit can be a part of the surgical guide means and/or of the positioning unit and/or of the attachment unit. It is hereby preferred, that the referencing unit is a part of the attachment unit, since the attachment unit emerges directly near the anatomical structure, which causes the referencing unit to be realised close to the anatomical structure. This can increase the quality and the success of the surgery.

If the referencing unit is attached to the positioning unit, the position of the positioning unit can be determined advantageously directly and hence a zero balance, which defines the start position for adjustment of the positioning unit, is determined. When realizing the referencing unit as a part of the surgical guide means it is especially advantageously that the surgical guide means can be coded separately. This coding can also be done for the positioning unit and the attachment unit with the markers.

In the case where calibration markers are set on the mobile part of the positioning unit only and there is no referencing unit on the fixed part nor on the attachment part, then it is necessary to know the previous values of each screw length to compute the necessary screw length values to reach the target. Such knowledge can be acquired by the user who enters data in the computer of the control unit or by using a ruler in the adjustment unit that measures screw lengths when it is in contact with the positioning unit.

In another embodiment of the invention, the calibration markers can be primarily be manufactured with X-ray visible and/or MRI visible material. Hereby the calibration markers can be localised advantageously using X-ray or MRI imaging methods, thus allowing determining the position of the referencing unit.

In another embodiment of the invention, the calibration markers can be primarily manufactured with X-ray invisible and/or MRI invisible material. Hereby the calibration markers can be localised advantageously with a higher contrast with respect to the other parts of the positioning unit. Furthermore the determination of the calibration markers can become easier.

In order to obtain a detailed image data set, the computer can straighten the image data and correct for image distortion. Therefore the computer can determine the relative positions of the different calibration markers between each other and hence establish the correction parameters accordingly.

In another embodiment of the invention, the referencing unit can feature several referencing units. Each referencing unit can carry out the position determination based imaging method analogue to the function of the referencing unit. Hereby several positions for the surgery guide means can be determined with one or several images in an advantageously way, such that these positions can be determined independently. Hence it is especially realisable that in case of several fractures or damages at different places at the spine, an intervention is carried out with one data set that has been acquired with an imaging system.

In another embodiment of the invention the positioning unit can be attached in a defined way at different locations on the attachment unit. Hereby the workspace can be increased in an advantageous way.

In another embodiment of the invention, the positioning unit can encompass means for angle detection. Hereby the position and/or the orientation of the positioning unit can be determined especially in an advantageous way. This can increase the safety for the patient.

In another preferred embodiment of the invention, the positioning unit can feature a readable scale or ruler. This allows increasing the safety for the patient, since the surgeon can verify the data.

In another embodiment of the invention, the positioning unit can be designed in a modular way. Hereby the positioning unit can be advantageously assembled in a reduced workspace, since the positioning unit can be made of parts/modules of different sizes thanks to the modularity.

Furthermore, the task can be achieved by a surgical positioning system, whereas the surgical positioning system comprises a surgical positioning unit according to the former description and an adjustment device. The adjustment device can be in particular designed as a wireless screwdriver. Furthermore the adjustment device is used for adjusting the positioning unit. By acting of the adjustment device on a screw of the positioning unit, the positioning unit can be designed to be adjustable.

Advantageously the adjustment of the positioning unit can be controlled by the user thanks to the adjustment device. Hereby the speed of the adjustment can be carried out depending on the pressure. As soon as the target position of the screw has been reached, the adjustment for this screw can be stopped.

In another embodiment of the invention, the adjustment device can act on the positioning unit in a coded way. Acting in a coded way shall mean that acting or correspondingly activating the screw can only occur if the coding allows it. Hereby a wrong activating or a wrong order while adjusting the screws can be avoided.

Hereby especially a signalisation for the user can be achieved by the coding, in particular if the correct actuator element is activated. This can be especially displayed by LED or display. Additionally the display could show the advancement of the adjustment that means for instance the number of remaining revolutions or turns of the screws.

In a further embodiment of the invention, the coding or identification of screws can be implemented electrically and/or mechanically and/or optically. Hereby especially the electrical coding can be realized by RFID chip or resistor coding implemented with defined areas of materials with different conductivity. The mechanical coding comprises different attachments on the adjustment device, whereas the attachments mechanically coded can be associated to certain screws. This corresponds to the key-lock system.

Furthermore the mechanical codings can have different surface designs or different hexagonal cavities. The coding can be in particular designed in such a way that several features are captured simultaneously for identification. The redundant coding can have the advantage, that the possibility of a wrong coding is minimized (e.g. in case of pollution of the coding, a wrong mechanical depth or a wrong resistance could be measured).

In another embodiment of the invention the adjustment can be carried out relatively to a stationary not moving part. Hereby it can be determined in a advantageous way, how many (partly) revolutions a screw has been turned relatively to a defined angle The optical codings could be colour differences or barcodes or areas scanned by a laser which once read can be associated to a screw.

In order to determine the position of the screws, the screws can comprise another coding, whereby a relative adjustment is feasible. In particular this can be performed in such a way that next to a screw a boring is placed with an angle ALPHA. Hereby the screw can complete several entire revolutions and/or a partial revolution with respect to the zero angle (ALPHA).

In order to achieve surgical security and a higher quality of the intervention, the coding can be designed in a redundant way. This can be accomplished in particular by two coding systems (e.g. optical and electrical).

In another embodiment of the invention, the surgical positioning system can comprise a computer, whereby there is a software running on the computer, whereby the software displays the image data and an operator defines or determines accordingly a position for the surgical guide means and the software determines screw parameters for the positioning unit with respect to the referencing unit. These screw parameters can be transferred to the adjustment device which thus can position the screws of the positioning unit.

Hereby the operator can exactly determine the position of the trajectory that constitutes a target to reach. Furthermore the data that were determined can be stored electronically for quality assurance. Not only the surgeon who takes responsibility for the intervention is considered as the operator as a single person but it can also be a team of persons being involved in the surgery and where each person only realizes a certain sub task. Meant are those persons that are involved in the success of the here described activities, steps and features.

Furthermore the task is achieved by a method for aligning of surgical guide means, whereby the former described surgical positioning system is used and whereby the method comprises the following steps:

- Attaching the surgical positioning unit to the anatomy in particular by clamping and/or tightening with screws of the attachment unit to the spine or an anatomical structure.
- Performing the medical imaging, in particular establishing multiplanar X-ray images and/or establishing of a volumetric data set, whereas at least parts of the referencing unit as well as of the bone to be treated are imaged
- Transferring of the dataset to the computer and determination of the pose of the surgical guide means by the operator and determining the position of the referencing unit and a set of corresponding screw parameters for the positioning unit.

By attaching the surgical positioning unit to the anatomy, a rigid basis for parts of the positioning unit can be established.

By the fact that parts of the referencing unit and parts of the treated bones are available in the computer thanks to the imaging, the operator can determine the optimal trajectory for his intervention and these data can be used for computing the positioning unit. Furthermore the computer can perform hereby the referencing automatically.

The last described step can be performed also in another advantageous order. Thereby the transfer of the data set is done first, then the determination of the pose (position) of the referencing unit by the computer, subsequently a definition of the desired pose (position) of the surgical guide means and at last the determination of a set of corresponding screw parameters by the computer.

In a further embodiment of the method, the step of connecting the surgical positioning unit to the anatomy can comprise the following further steps: attaching the attachment unit to the anatomy, attaching the referencing unit to the attachment unit and attaching the positioning unit to the referencing unit and/or to the attachment unit, whereas the last step can also be carried out later in the course of the method. By this further step of connecting the surgical positioning unit to the anatomy can be advantageously further divided and hence the quality of the surgery can be increased. Hereby, the adjustment of the positioning unit can be performed advantageously not at the patient directly.

In a further embodiment of the method, the method can comprise the step of transferring the screw parameters to the adjustment device. Hereby the screw parameters can be advantageously stored in the adjustment device.

In a further embodiment of the method, the method can comprise the step of adjusting the positioning unit by the adjustment device. Hereby, errors occurring during transmission of the position data for the surgical guide means can be reduced. Preferably the data can be transferred in the computer connected to the positioning unit. The adjustment device can subsequently adjust the positioning unit accordingly. Hereby the adjustment device can preferably designed mobile in order to move it to the positioning unit.

In order to carry out an exact adjustment, the screws can be turned first into one direction until bedstop and then moved in the other direction until reaching the target parameter.

In order to gain good access to a concerned bony structure, exposing of the necessary bony structures can be done prior of attaching the surgical positioning unit to the anatomy. Exposing of the necessary bony structures can be advantageously be performed by the surgeon.

Preferably, the method can comprise the following steps in the following preferred order:

- The referencing unit is attached for the imaging methods
- The referencing unit is removed.
- The parameters are determined by the computer
- The positioning unit is adjusted
- The positioning unit is attached to the attachment unit In a preferable embodiment, the adjustment device identifies the screw to which it is attached by the coding of the screw before the adjustment of said screw.

The expert can according to requirements of the intervention modify this preferred order without altering the scope of the invention.

BRIEF DESCRIPTION OF THE DRAWINGS

In the following the invention is further explained by examples of different embodiments, in reference to the following figures, wherein.

DETAILED DESCRIPTION OF THE INVENTION

Adjustment Device

Figure 1:
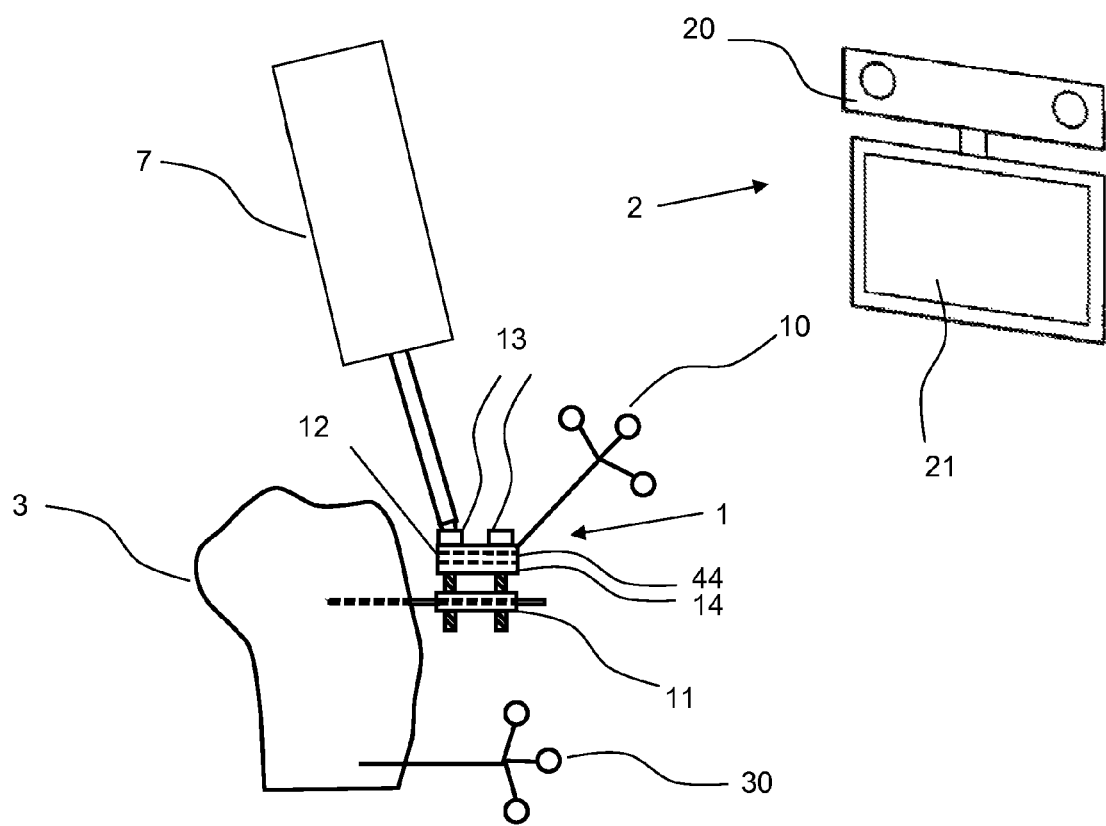
FIG. 1 is a sequential view showing a conventional screwdriver positioned into the screws of a surgical instrument.
Figure 2A:
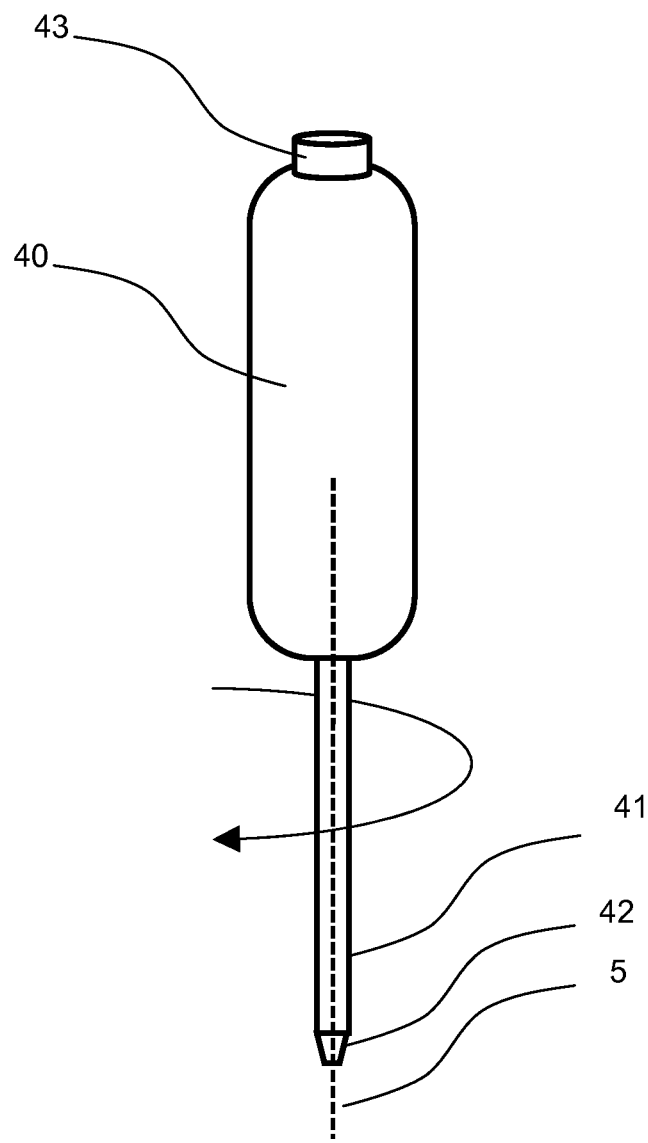
FIGS. 2A and 2B show the adjustment device according to the invention.

As represented on FIG. 2, the adjustment device 4 according to the invention is an actuated screwdriver that comprises a body or handle 40, a stem 41, a tip 42, an optional button 43 that is activated by the user, and an encapsulated battery that brings enough power to rotate the screwdriver.

In a preferred embodiment, the actuation of the screwdriver is done by a motor. In a preferred embodiment the motor is a brushless motor which directly provides feedback on number of turns performed using its internal coding system. But alternatively many other solutions of actuators can be used to rotate a screw, such as piezoelectric actuators. The screw can be replaced by any non reversible linear motion mechanism, such as hydraulic or pneumatic mechanism, and the actuator can be any device that provides a linear motion of said mechanism.

Figure 3A:
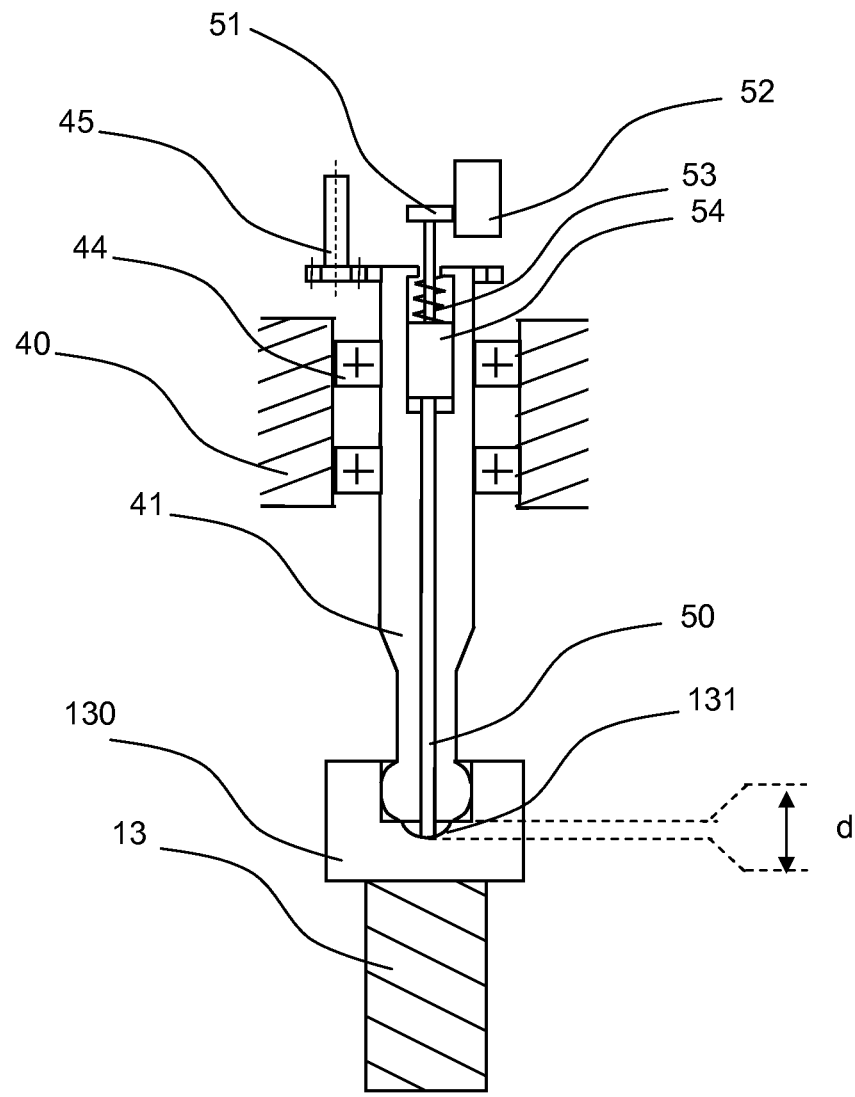
FIG. 3A is a partial sectional view of the device stem, device tip, and instrument screws, where the auto-detection of the screw is done by a mechanical solution.

As better seen on FIG. 3A, the stem 41 is rotating with respect to the device body 40 thanks to a rolling system 44. The rotation is controlled by a motorized system 45. It must be noted that the devices illustrated on FIGS. 4 to 7 also comprise said rolling and motorized systems, although these features are not shown on these figures.

The device is controlled by the control unit 21 of the navigation system or by the control unit of the imaging system, depending on the way the position of the instrument is determined. The controlled parameters are: turn direction, number of turns, turn speed, turn acceleration and stop. The number of turns and the direction are parameters given by the computer and transmitted through the wireless protocol to the device.

The device communicates with the computer through a wireless protocol, such as Wifi or Bluetooth or ZigBee. In one preferred embodiment, the wireless communication is based on the Bluetooth communication protocol. Optionally, the communication can be also performed by standard wires with a standard wire and communication protocol such as USB, Ethernet, IEEE 1394, RS232, or a proprietary wire and communication protocol, and in that case the power supply is also brought by a cable.

In a simple embodiment of the invention, the computer display indicates to the user the screw in which the screwdriver must be placed. When the user has placed the screwdriver in the head of the screw indicated on the screen, the user presses a button and the screwdriver moves the screw to the target position. The operation is repeated for each screw. If the user misses one screw the computer display shows which screw must be readjusted until the final position of the guide matches the target. For instance, the screw that has the most important number of turns to be accomplished is suggested to the user. Or the screw are always adjusted in the same order, starting by screw 1, then 2, until screw N and the process is iterated by skipping screws that already reached the target position with a predefined limit.

Depending on the kinematic structure (e.g. containing singularities) some screws will have to be adjusted more than once in a defined order.

In the case of the adjustment of a drill guide (see FIGS. 11, 12, 16), the calculated data are transferred to the device 4. Using a RFID identifier, a single screw (corresponding to one degree of freedom) can now be adjusted in a defined way with the adjustment device in the positioning unit. Once all degrees of freedom are adjusted this way, the drill guide 15 is aligned optimally to a target defined on images and a defined drilling can be carried out.

Figure 2B:
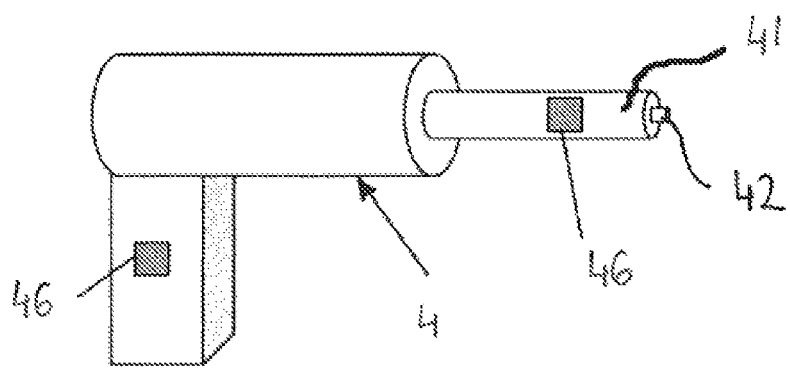
Figure 3B:
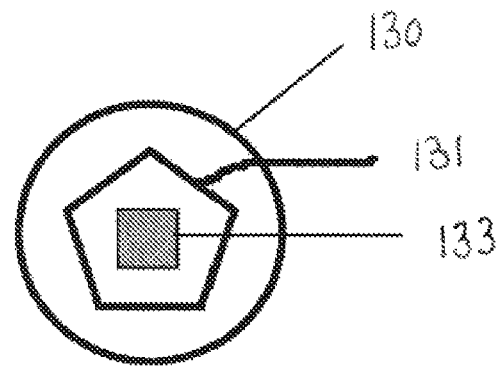
FIG. 3B is a view of the screw head adapted to recognize the tip of the adjustment device.

FIG. 2B shows additionally a possible type of coding. Using the identifiers 46 the correct device 4 or the corresponding correct stem 41 and tip 42 for the device 4 can be determined. This stem 41 engages in the screw head 130. The tip 42 engages into the screw head cavity 131 which comprises a mechanical resistor element 133. The coding is established by the shape of the screw head cavity 131 (see FIG. 3B).

The term screwdriver is used without loss of generality. It means an external mechanism to turn a screw in a given direction. It is also possible to use several mechanisms to grab the screw head by friction or pressure only when a go button is pushed so that the screw cannot be turned manually when the device comes in contact with the screw head, which eliminates parasite motions of the screw.

It is also possible to design a motorized screwdriver such that the handle contains only the stator part and the screw head contains the rotor part, or vice versa. In such mechanism, the handle of the screwdriver can be purely made of coils and it is easily covered by a sterile drape since it has no turning part. In this case, the screw head is a set of miniature coils.

There exist many other adjustment devices principles that can be used to turn the screw with a handy device.

Automatic Detection of the Screw ID

Advantageously, the adjustment device comprises detection means for determining the identification (or code) of the screw the tip is in contact with. Depending on the various embodiments disclosed below, each screw possesses within the navigation system identification (ID) means to distinguish it from the others.

In one preferred embodiment, illustrated on FIG. 3, the adjustment device detects which screw the tip is in contact with by a mechanical solution. To that end, a thin rigid mechanical stem 50 is sliding inside the device stem 41. By using the rigid mechanical link between the stem 50, the body 54, and the position cursor 51, the contact between the sliding stem 50 and the screw's head cavity 131 determines the value of the position sensor 52. When the tip is not inserted into the screw's head 130, a spring 53 places the position sensor 52 at its default position. When the tip is in the screw's head 130, the position sensor 52 measures the depth d of the screw's head cavity 131. This depth is measured and transmitted to the control unit of the navigation system 2 by the wireless communication. Each screw's head cavity 131 has a different depth d, so that the position sensor delivers a different value for each screw, allowing the control unit of the navigation system to know which screw the device is about to activate.

Figure 4:
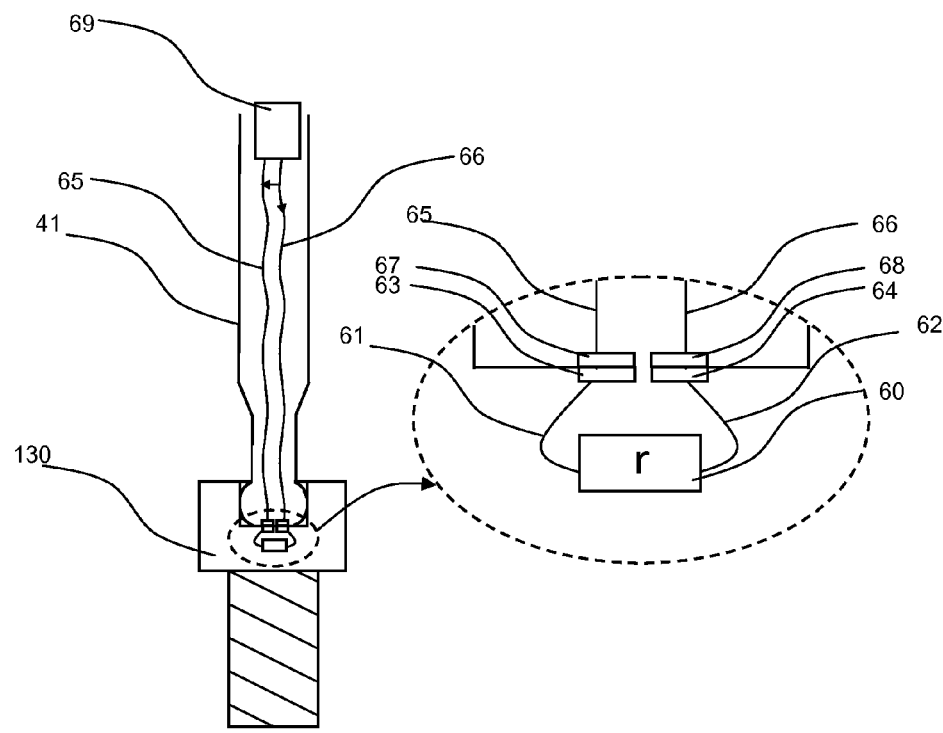
FIG. 4 is a partial sectional view of the device stem, device tip, and instrument screws, where the auto-detection of the screw is done by an electrical solution.

In another embodiment, illustrated on FIG. 4, the adjustment device detects which screw the tip is in contact with by an electrical solution. In this case, a resistance 60 is inserted into the screw's head 130 linked by two electrical wires 61, 62 respectively to two connectors 63, 64 that are on the bottom surface of the screw's head. In the device stem and tip are inserted two electrical wires 65, 66 that are respectively connected to two connectors 67 and 68 that are on the extremity of the device tip. When the tip is in the screw's head 130, the connectors 63 and 67 are in contact, as well as the connectors 64 and 68. It allows the device to measure the tension thanks to an ohmmeter 69. This tension is measured and transmitted to the control unit of the navigation system by the wireless communication. Each screw's head has a different resistance value r, so that the ohmmeter 69 delivers a different value for each screw, allowing the control unit of the navigation system to know which screw the device is about to activate.

Figure 5:
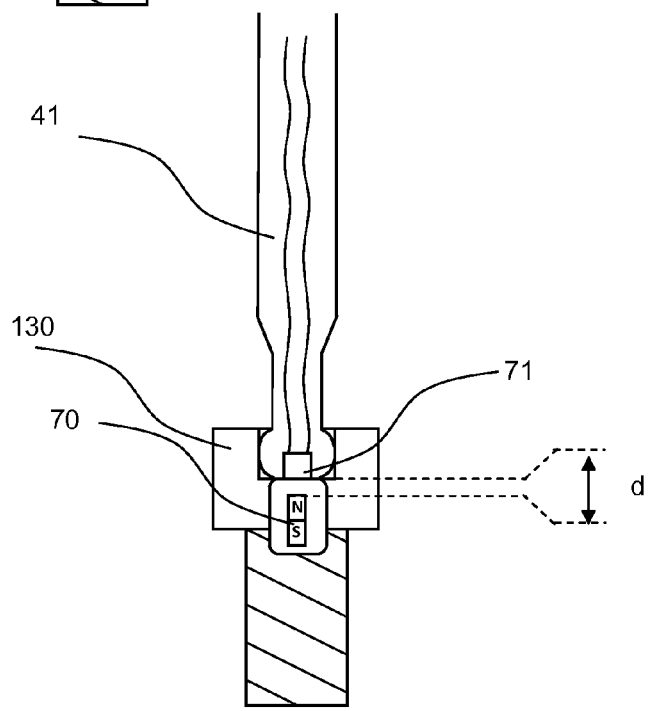
FIG. 5 is a partial sectional view of the device stem, device tip, and instrument screws, where the auto-detection of the screw is done by a magnetic solution.

In another embodiment, shown on FIG. 5, the adjustment device detects which screw the tip is in contact with by a magnetic solution. A magnet 70 is inserted into the screw's head 130. A "Hall effect" sensor 71 is inserted into the device tip that delivers a tension that is dependent of the distance between the magnet 70 and the sensor 71. This tension is measured and transmitted to the control unit of the navigation system by the wireless communication. Each screw's head has the same magnet but inserted at a different depth d, so that the sensor 71 delivers a different tension for each screw, allowing the control unit of the navigation system to know which screw the device is about to activate.

Figure 6:
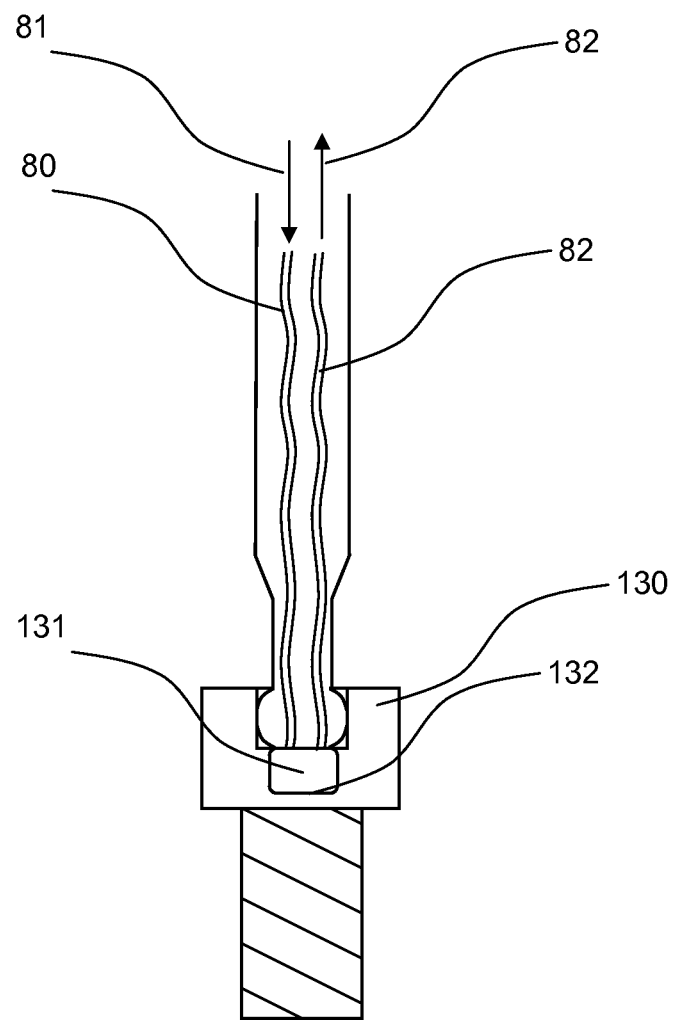
FIG. 6 is a partial sectional view of the device stem, device tip, and instrument screws, where the auto-detection of the screw is done by an optical solution.

In another embodiment, illustrated on FIG. 6, the adjustment device detects which screw the tip is in contact with by an optical solution. To that end, a cavity 131 is inserted into the screw's head 130. The bottom 132 of the cavity 131 is painted with a uniform color or with a pattern such as a bar code. A first optical fiber 80 carries light 81 from the device stem to the cavity 131, in order to light the cavity 131. A second optical fiber 81 carries the light 83 from the cavity to the device stem and then to an optical sensor such as a micro camera (not shown). The image delivered by the second optical fiber 82 is transmitted to the control unit of the navigation system by the wireless communication. Each bottom 132 of screw's head cavity 131 has a different color or different pattern, allowing the control unit of the navigation system to know which screw the device is about to activate.

Figure 7:
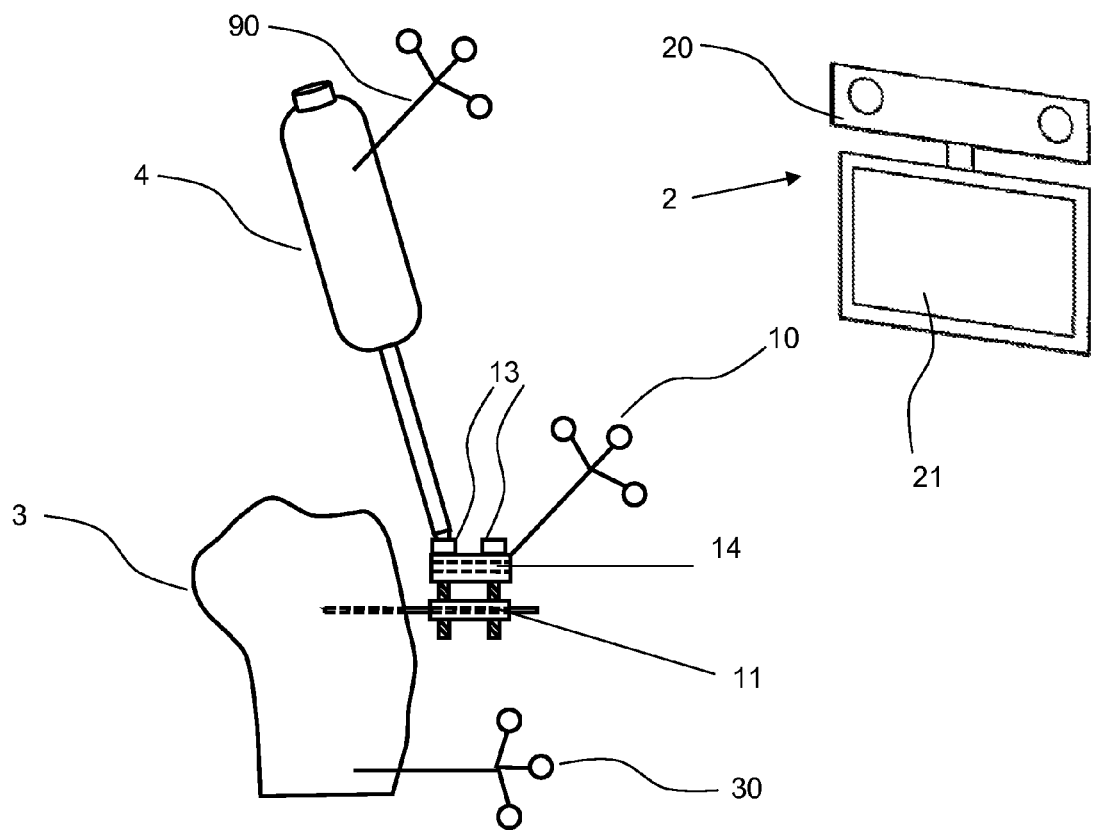
FIG. 7 is a sequential view of the adjustment device, the navigation system, and the instrument, where the auto-detection of the screw is done by a tracking solution.

In another embodiment, shown on FIG. 7, the adjustment device detects which screw the tip is in contact with by a tracking solution. A tracker 90 is rigidly fixed to the device 4. One knows by design the device tip position in the device tracker 90 coordinates system. One knows by design the screw's head position in the instrument tracker 10 coordinates system. Then, once the device tip is inserted into a screw's head, the control unit of the navigation system 2 can determine which screw's head the device tip is inserted in, allowing the control unit of the navigation system to know which screw the device is about to activate. If the accuracy of the navigation system is not sufficient, it can be compensated by adding a simple mechanical contact sensor that detects that the tip is in contact with the screw head.

In another embodiment (not illustrated here), the adjustment device detects which screw the tip is in contact with by a software solution: before the device activation, the navigation system records the position of the Instrument, called the initial position. When the user presses the activation button, the device turns as first step the stem in a constant known direction (e.g. clockwise). The navigation system then tracks the movement of the mobile part of the instrument. By taking into account the design of the screw, the design of the Instrument, the given rotation direction and the number of turns that were applied, one can determine the unique screw that brought the instrument to this current position. Then, once the screw ID is determined by this first stem actuation, the device can then rotate the stem in the correct rotation direction with the correct number of turns to reach the target position.

In all that precedes the control unit of the navigation can be replaced by the control unit of the imaging system, if a medical imaging system is used instead of a navigation system to define the target of the positioning unit.

Surgical Procedure Flow Diagram (with Navigation)

Figure 8:
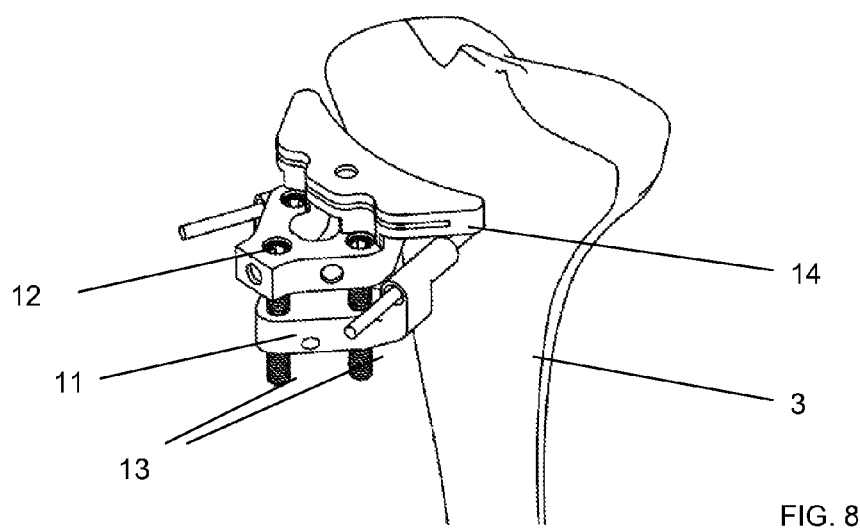
FIG. 8 illustrates a cutting slot which is adjusted by three screws with respect with the fixed part fixed to the tibial bone.
Figure 18:
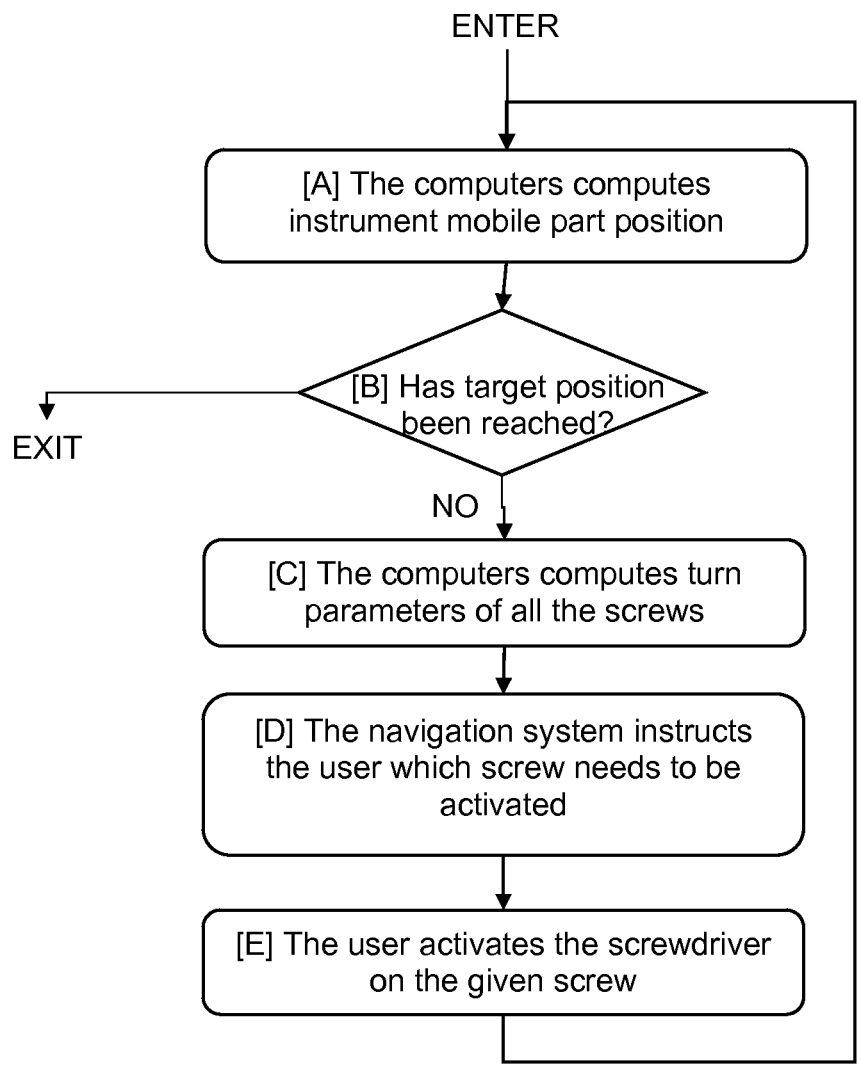
FIG. 18 is a surgical procedure flow diagram, showing how the surgeon is supposed to interact with the navigation system to adjust the desired instrument position.

In the example where a navigation system is used, the surgical procedure flow diagram for adjusting the position of a cutting plane as shown on FIG. 8 is composed of steps [A], [B], [C], [D] and [E] that are described in FIG. 18.

[A] The control unit 21 computes the current position of the mobile part 12 of the positioning unit with respect to the solid 3 thanks to the instrument tracker 10, the solid tracker 30, and the localizer system.

[B] If the current position is the target position then the procedure exits.

[C] If the target position is not reached, then for each screw 13$i$, where i is equal to 1, 2 or 3, the computer computes the unique number of turns Ti that needs to be applied on 13$i$, so that the mobile part 12 reaches the target position. Ti is positive if the rotation direction is clockwise and negative if the rotation direction is counter-clockwise. For that computation, the computers needs to know the target position of the instrument, which is selected by the surgeon, the screws parameters (diameter, thread length, thread thickness), which are known by design, the screws positions on the Instrument, which are known by design.

[D] The navigation system instructs the user which screw needs to be activated:

i. In one preferred embodiment, the user is instructed to place the device tip 42 on a given screw's head. The computer displays on the screen which screw's head the device tip 42 must be placed on. In one preferred embodiment, each screw's head has a unique color, and the computer displays the color of the screw on the screen. In another embodiment, each screw's head is labeled with a unique number (such as 1, 2, 3), and the computer displays the number of the screw on the screen. In another embodiment, each screw's head is labeled with a unique letter (such as A, B, C), and the computer displays the letter of the screw on the screen. Screws can be also differentiated simply by their position on the instrument or by their shape. The user needs to follow the screws order displayed by the computer.

ii. In another preferred embodiment, the user is instructed to place the device tip 42 on a given screw's head. Each screw's head has a unique characteristic such as color, or number, or letter as detailed in (i). The computer computes on which screw's head the device tip 42 must be placed on. The information is then transferred from the computer to the device by the wireless communication protocol. The device then instructs the user by displaying the information on itself, preferably on the top of the handle of the screwdriver. It can be by lighting some colored LEDs if screws are identified by a color, by lighting a letter if screws are identified by a letter, or by lighting a number if screws are identified by a number. The user needs to follow the screws order displayed by the computer or displayed on the handle of the screwdriver.

iii. In another preferred embodiment, the user is not instructed to place the device tip 42 on a particular screw's head. The user can independently choose any screw's head, whatever the order is. The device detects when the tip is in contact or not of the screw's head, and detects which screw it is in contact with, and communicates the screw ID to the navigation system by the wireless communication protocol such that the adjustment necessary for that particular screw is known. Alternatively, these parameters can be first stored in the driver.

[E] Then the user presses the button 43 to activate the adjustment device. If the device is used with automated detection of contact and identification of screw head, pressing a button is not necessary and the device is activated automatically. The device stem 41 then turns the given number of turns Ti that was determined by the computer to reach the target position of the instrument. Once the device stem 41 has turned the desired number of turns Ti, the stem rotation stops, instructing the user that the target position for the screw 13*i* has been reached. Optionally, the navigation system 2 can check that the mobile part 12 has reached the desired position for that particular screw and if it is not the case, send an updated command to the screwdriver to add more portions of turn in order to adjust it accordingly and this process can be repeated until the position of the mobile part 12 has reached the desired position within a given arbitrary accuracy such as 0.2 mm for instance, which is done like a standard servoing mechanism. Then the instrument position is updated and the process goes to step [A] for setting other screws to the desired positions. The global process is iterated until all screws have reached their desired position such that the mobile part is now in its final target position for all desired degrees of freedom.

To reach a target screw position, there exist many possible methods to control the motors in order to optimize the speed of the process:

A first method consists in measuring the position of the mobile part before the screw has reached its final position using the navigation system and iterating the command on the motors that take into account the measured position and the target position. Standard control commands can be used to optimize the speed and convergence of such process, for instance using well known Proportional Integral Derivative (PID) commands.

Another method consists in turning the motor in the right direction with an increasing speed and then decreasing speed when the motors reach the expected position and finally stopping the motor when it is very low speed so that the measurement taken with the navigation system can be done with averaging and the time delay to stop the device is compliant because of low speed.

There exists many additional ways of optimizing the command by using the measurements of the final position of the mobile part using navigation system or by using the measurements of the motor controller that often provide the number of turns performed by the motor, with a division of such number by mechanical reduction. It is also possible to combine both measurements in real time in order to optimize and stabilize the convergence towards the target position.

In some situations, the relationship between the screws is not independent, and it is therefore necessary to adjust some screws before adjusting other screws and coming back to the first screws to be able to reach the desired target. The system can easily predict those situations and optimize the paths between those maneuvers to limit the number of iterations.

Parallel Architectures

In a preferred embodiment, the positioning unit that is used in conjunction with (a) a navigation system or (b) a referencing unit and medical images uses a parallel mechanical architecture instead of a serial architecture.

The advantage of a parallel architecture is the stiffness of the positioning unit such that the mobile part on which the guide or instrument is mounted has a stable relationship with respect to the anatomical structure for any position of the screws that activate individual degrees of freedom of the parallel architecture.

A drawback of a parallel architecture is that it is usually difficult to adjust the screws manually and individually to reach a desired global position because each screw influences all parameters of the global position. Degrees of freedom are strongly correlated together.

However, using the adjustment device which positions automatically the screws to a defined position determined by the computer eliminates this drawback and only the advantageous aspects of this architecture remain.

Manual Adjustment

In a backup mode of functioning, the computer of the control unit simply displays to the user the number of turns to be applied on each screw.

In a preferred embodiment, a ruler can be attached permanently or temporary to each screw to make it possible the adjustment of each screw without the adjustment device. The ruler can be integrated to the positioning unit (see FIG. 16) or can be provided directly on the screwdriver.

EXAMPLE 1

Spine Surgery with Medical Imaging

According to a first advantageous embodiment of the invention, illustrated on FIGS. 9-12, the adjustment device can be utilized in spine surgery performed with medical imaging.

Figure 9:
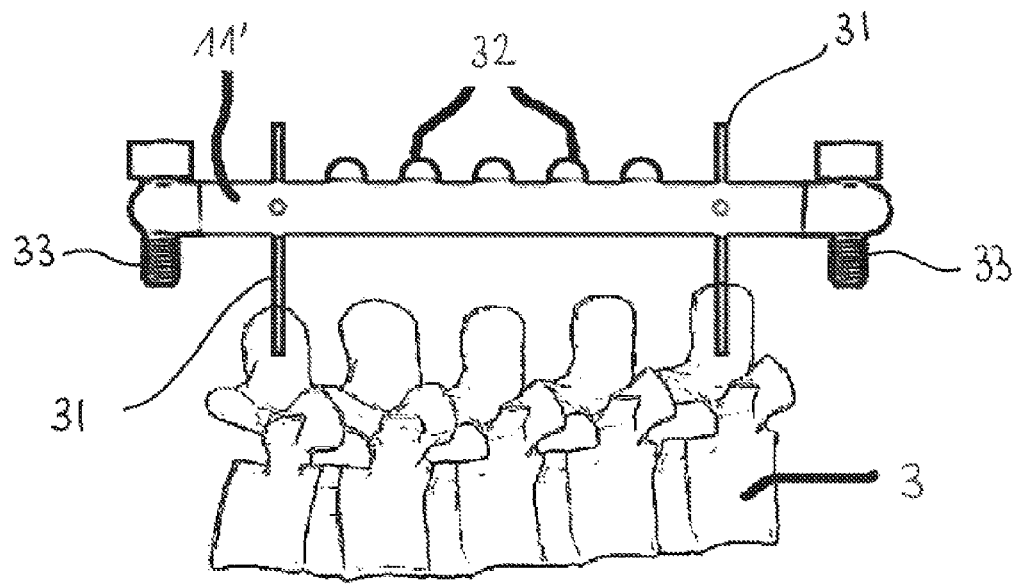
FIG. 9 illustrates an embodiment of the fixed part used in spine surgery.
Figure 9:
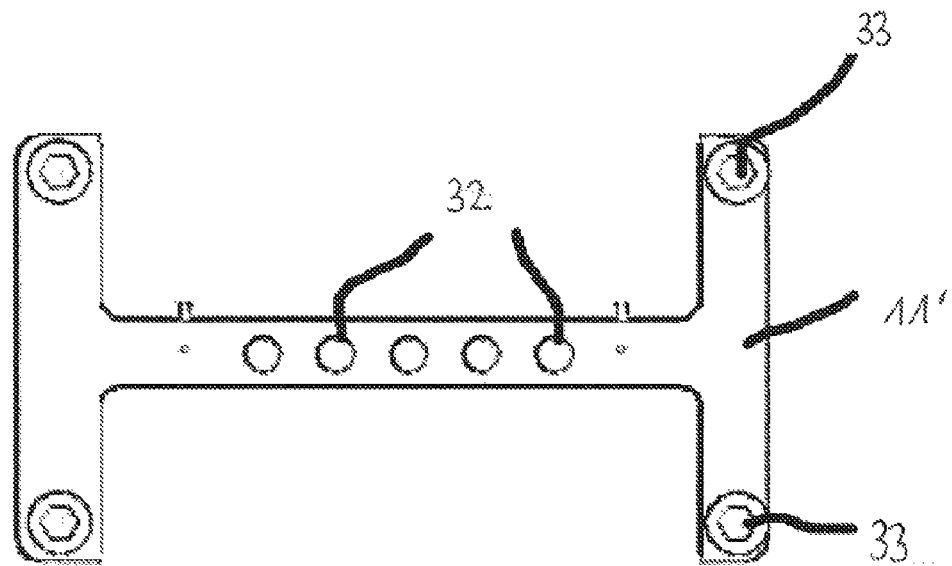

FIG. 9 shows a detail of a spine 3 with several vertebral bones.

An attachment unit 11', which can be seen on side and upper views, is an percutaneous support having a general H shape for supporting a positioning unit for a drill guide (not shown here).

The pins 31 are used for attachment of the attachment unit 11' to the spine 3.

Thanks to the flanges 32, different positions for the attachment of the positioning unit and/or the referencing unit (not shown here) are possible.

At the same time the flanges 32 can be used as X-ray visible markers.

Optionally, four screws 33 are used as an additional stabilization for support on the skin, whereas the screws 33 can be likewise designed as markers.

Figure 10:
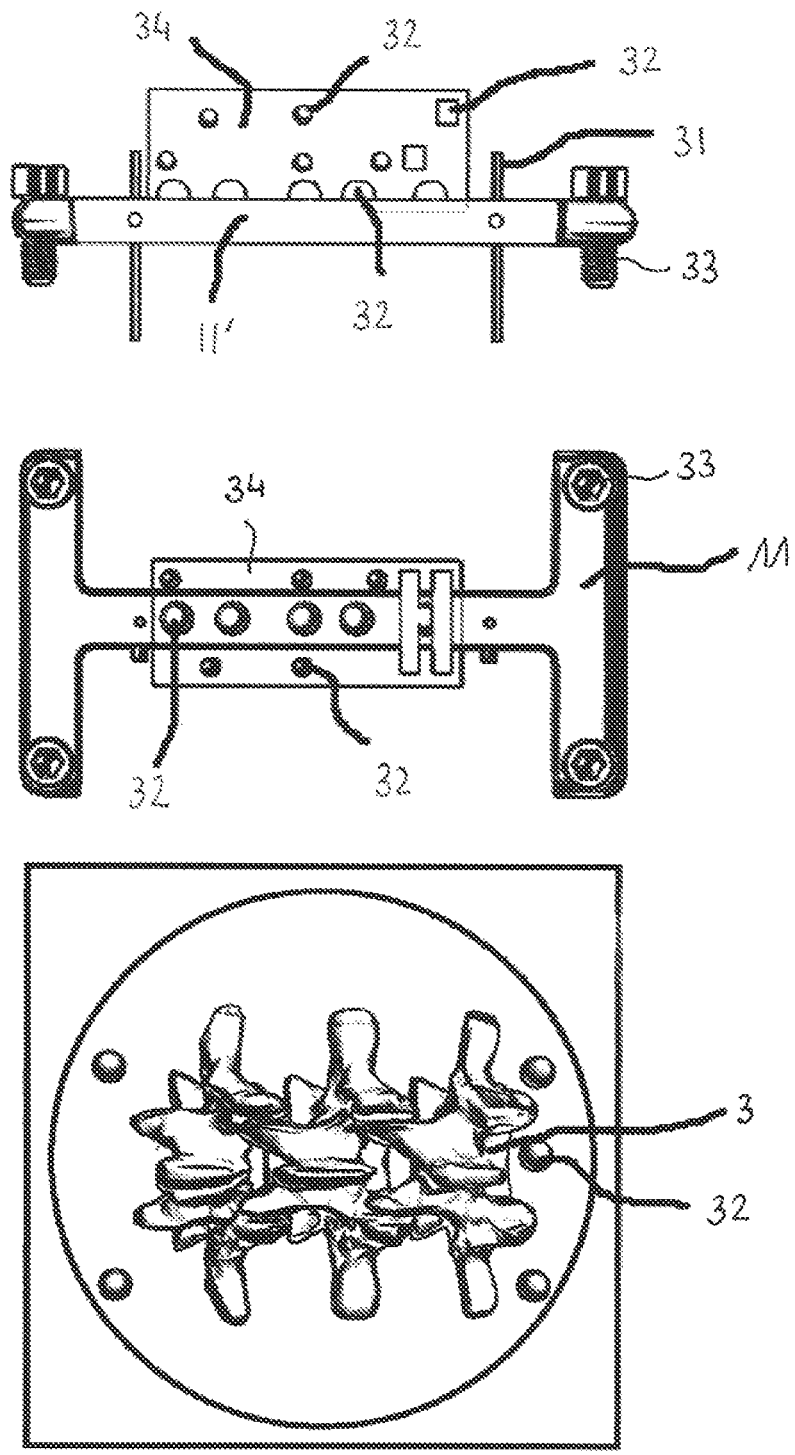
FIG. 10 illustrated the attachment of a referencing unit to the fixed part of FIG. 9.

FIG. 10 depicts an attachment unit 11' in different views.

The top view shows a referencing unit 34 that is attached orthogonally to the fixed part 11.

This orthogonal referencing unit 34 comprises among others also squared markers 32.

In the top and middle views it can be seen positioning points which are designed as markers 32.

The bottom view illustrates a x-ray image which shows the spine 3 and markers 32.

Figure 11:
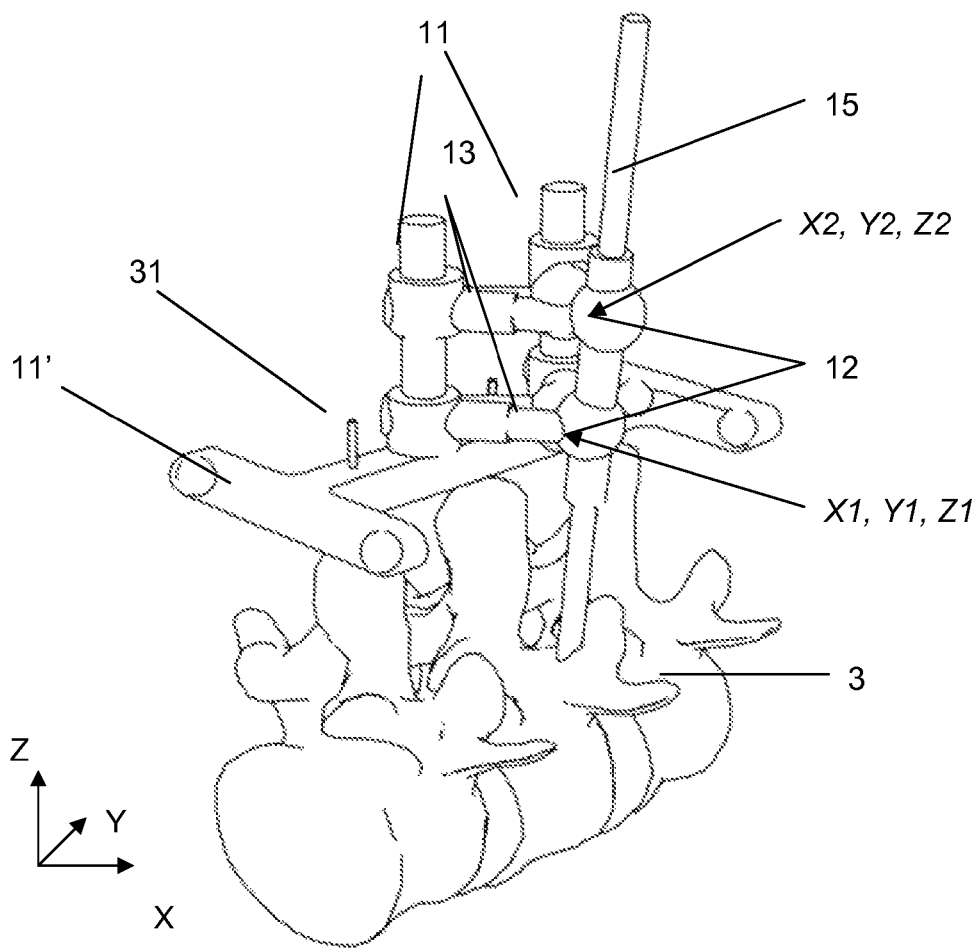
FIG. 11 is a view of the mobile part supporting a drill guide for spine surgery that is adjustable by four screws.

FIG. 11 shows a surgical positioning unit which is located at spine 3.

The attachment unit 11' with the referencing unit 34 including the corresponding markers is flange mounted to the vertebrae via pins 31.

The fixed part 11 of the positioning unit is mounted on the referencing unit 34 (not shown here).

The actuator elements of the positioning unit are four screws 13 that can adjust the mobile part 12 and thus the drill guide 15 in a defined way.

The mechanism uses two pairs of screws 13.

A lower pair of screws 13 at fixed level Z1 moves a ball and socket joint 12 in a small plane to a defined target (X1, Y1) in a limited range that constitutes a first small two-degrees of freedom parallel architecture.

An upper pair of screws 13 at fixed level Z2 moves a ball and socket joint 12 in a small plane to a defined target (X2, Y2) in a limited range that constitutes a second small two-degrees of freedom parallel architecture.

The upper and lower pairs of screws 13 are connected on their basis and constitute a four-degrees of freedom positioning unit.

The drill guide 15 is passing through the two points (X1, Y1, Z1) and (X2, Y2, Z2) which define a linear trajectory. Acting on (X1, Y1) with the first pair of screws and on (X2, Y2) using the second pair of screws makes it possible to reach any linear target in a limited range.

To that end x-ray images are acquired for the entity shown in FIG. 11 and transferred to the computer.

Based on the markers determination, the position of the drill guide 15 can be determined.

For this the positioning unit (in zero position), the drill guide 15, the attachment unit 11' including referencing unit 34 with markers 32 and the displayed parts of the spine 3 have defined positions to each other.

In the present embodiment the operator has positioned the positioning unit already at the patient in such a way that the drill guide 15 must be modified only slightly.

Using the x-ray images available in the computer and the corresponding coordinates the operator determines the trajectory of the boring in the vertebra.

The computer computes the adjustments of the drill guide 15 using the coordinates such that the extension of the drill guide 15 coincides with the planned boring in the vertebrae.

Figure 12:
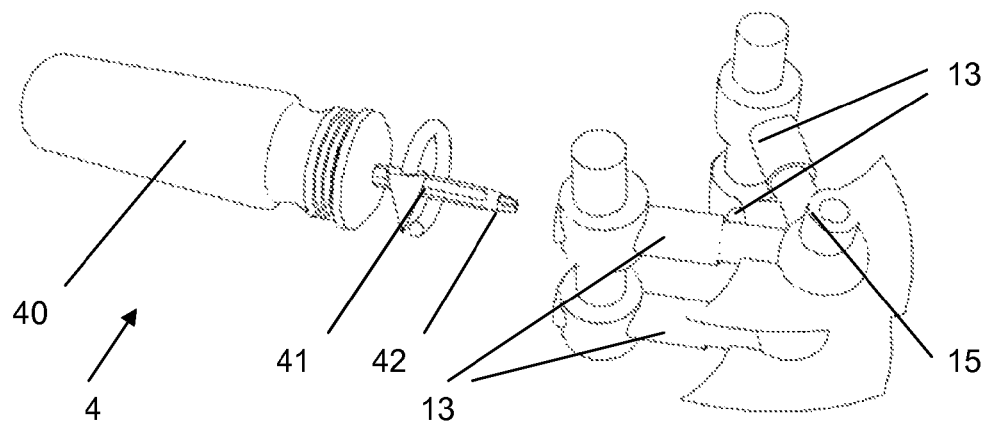
FIG. 12 is a view of the adjustment device operated with the mobile part of FIG. 11.

As shown on FIG. 12, the adjustment device 4 is then operated to turn the screws 13 by the appropriate number of turns.

Figure 13:
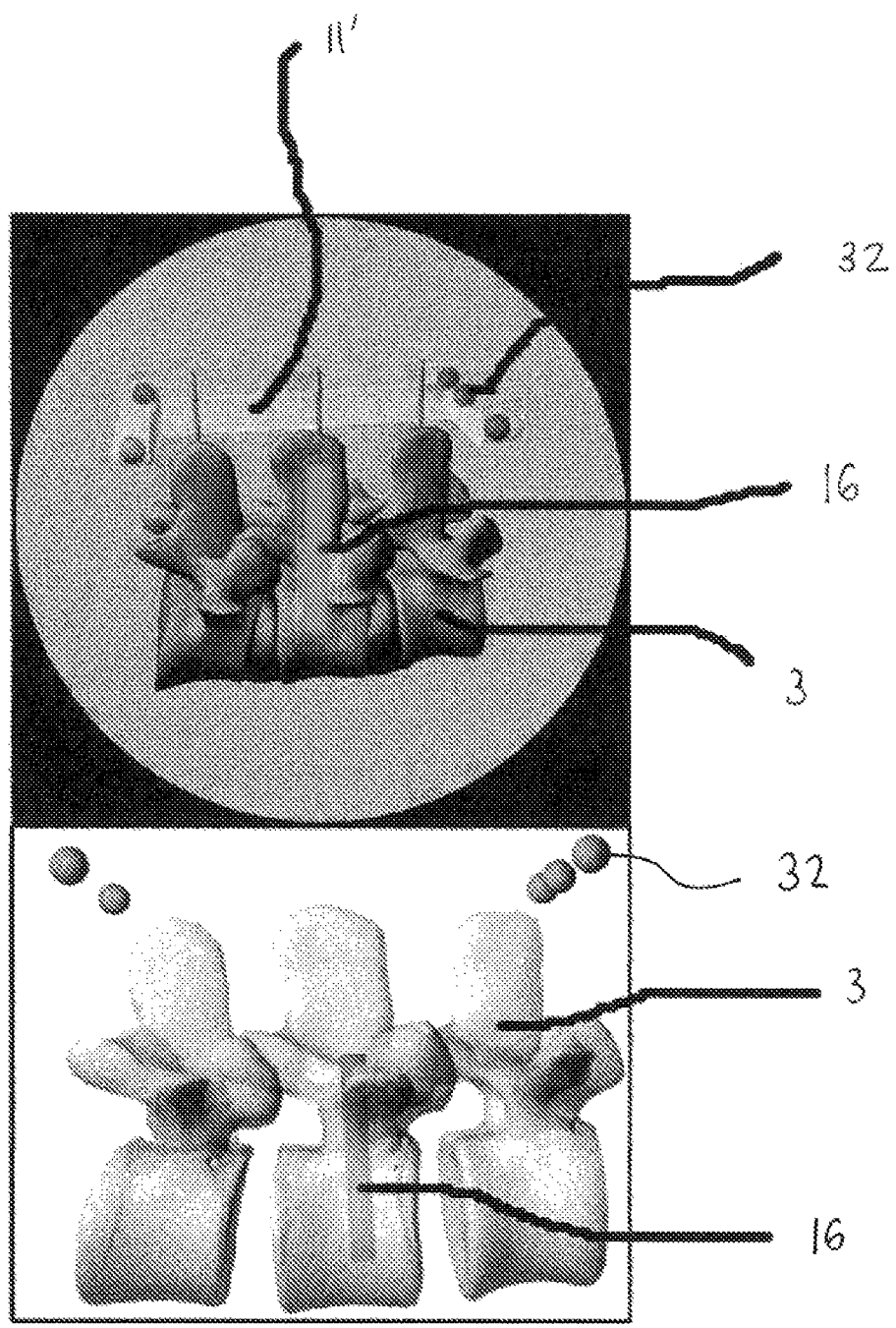
FIG. 13 illustrates x-ray images of the planned drill axis in a vertebra.

FIG. 13 shows an x-ray image of the attachment unit 11' and the planned drilling bore 16.

EXAMPLE 2

Hip Resurfacing Surgery with Medical Imaging

A second advantageous embodiment of the invention, illustrated on FIGS. 14-17, the adjustment device can be utilized in hip surgery performed with medical imaging.

For the use of the surgical instrument the positioning unit must be attached to the object being operated (here, the femoral head).

Figure 14:
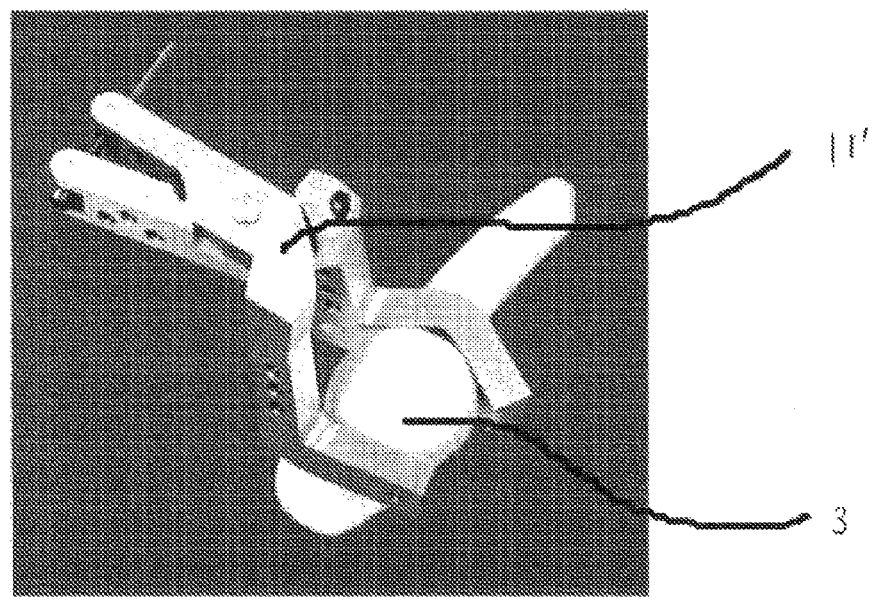
FIG. 14 shows an embodiment of the fixed part adapted for hip surgery.
Figure 15:
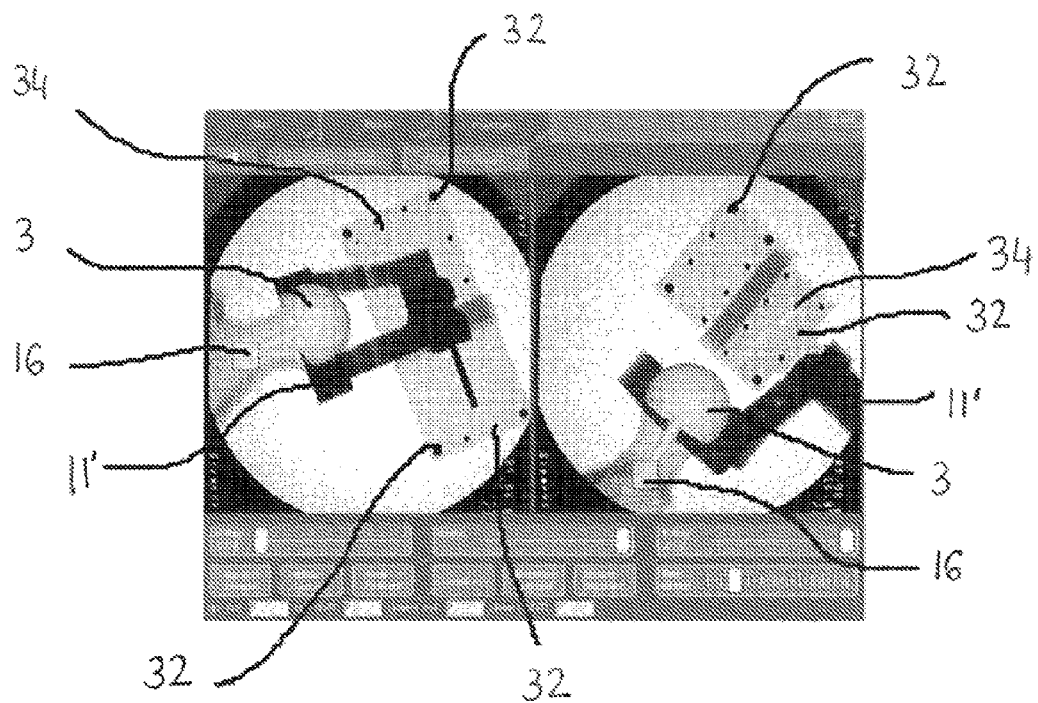
FIG. 15 is an x-ray image of the fixed part, a referencing unit fixed thereon

As one can see from FIGS. 14 and 15, this is achieved by a clamp mechanism which is implemented by the attachment unit 11'. The attachment unit 11' is flange mounted to the femoral head 3 of the bone, such that there is an essentially rigid connection.

As one can deduce from the x-ray image in FIG. 14, the referencing unit 34 is flange mounted to the attachment unit 11'. The referencing unit 34 comprises additionally x-ray visible markers 32, whereby two x-ray images (e.g. lateral view and frontal view) allow determining the coordinates in space.

There are further functions that can be implemented via the markers 32 in particular the flange mounting of a unit with screws. For that purpose a boring for example can act as an essentially x-ray invisible material. With this boring a flange mounting is possible with screws.

With the computer program shown in FIG. 15, the operator can define the exact trajectory of a boring 16 inside the bone or correspondingly in the femoral head 3.

Thanks to the coordinates of the referencing unit 34, which is designed as attachment unit at the same time, and the planned boring 16, the computer which hosts the software program can determine the adjustment of surgical guide means (not shown here) using the mobile part (not shown here).

Figure 16:
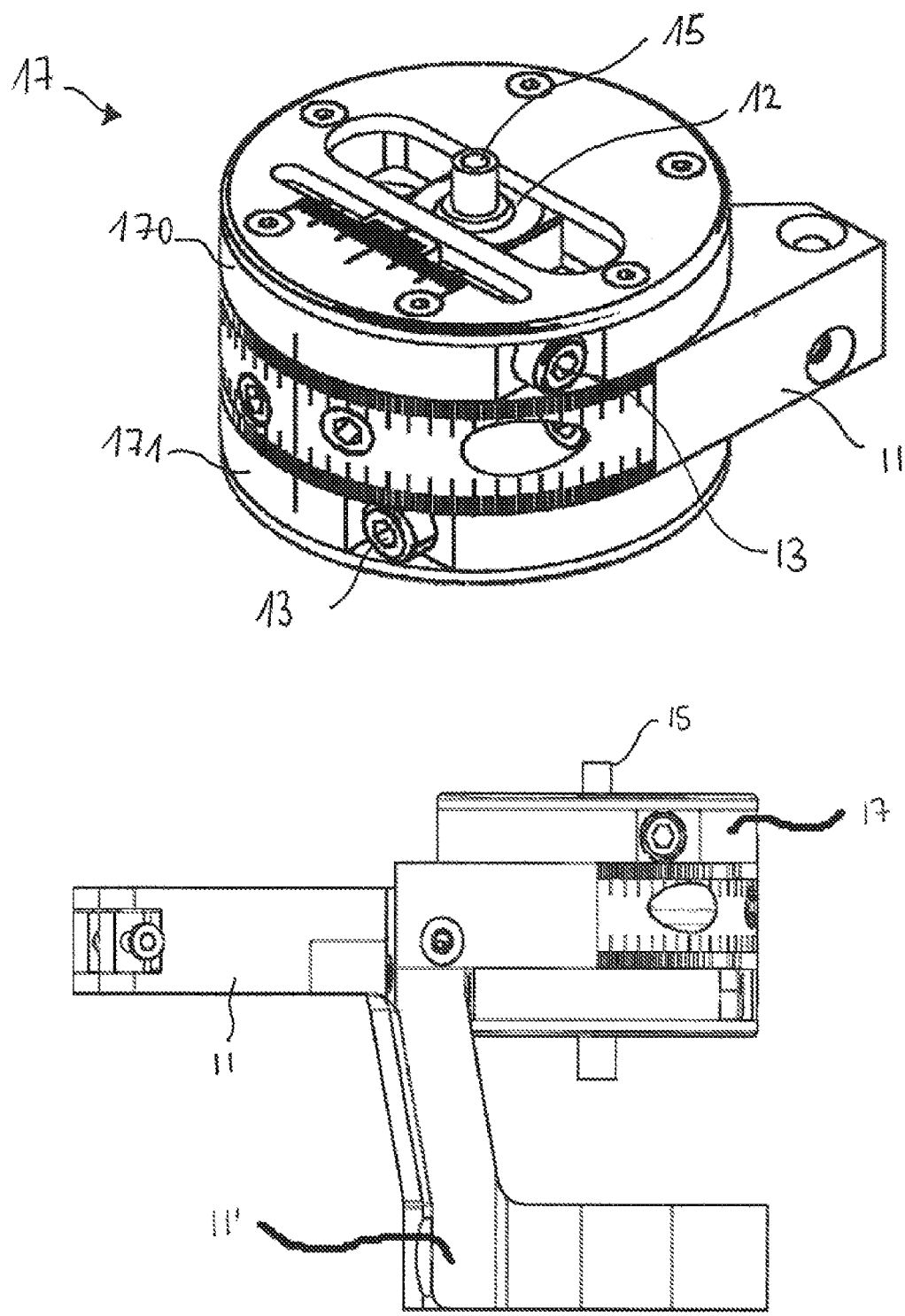
FIG. 16 is a positioning unit supporting a drill guide for hip surgery.

FIG. 16 shows a positioning unit 17 which comprises four degrees of freedom of adjustment for adjusting the surgical guide means (which is here a drill guide 15).

Such a positioning unit 17 has a scale used to target positions in a defined manner that were computed before by the computer.

The positioning unit 17 comprises a fixed part 11 that can be attached to the attachment unit, and a mobile part 12 that supports the drill guide 15.

The positioning unit 17 also comprises an upper plate 170 and a lower plate 171 and is provided with screws 13 that are able to move the mobile part 12 with respect to the fixed part 11, thereby modifying the position and orientation of the drill guide 15.

In order to guaranty high accuracy, all four adjustments for the different degrees of freedom are reset to 0.

FIG. 16 depicts the positioning unit 17 with the attachment unit 11' as a detachable unit (modular design) which is hence directly flange mountable to the bone.

Figure 17:
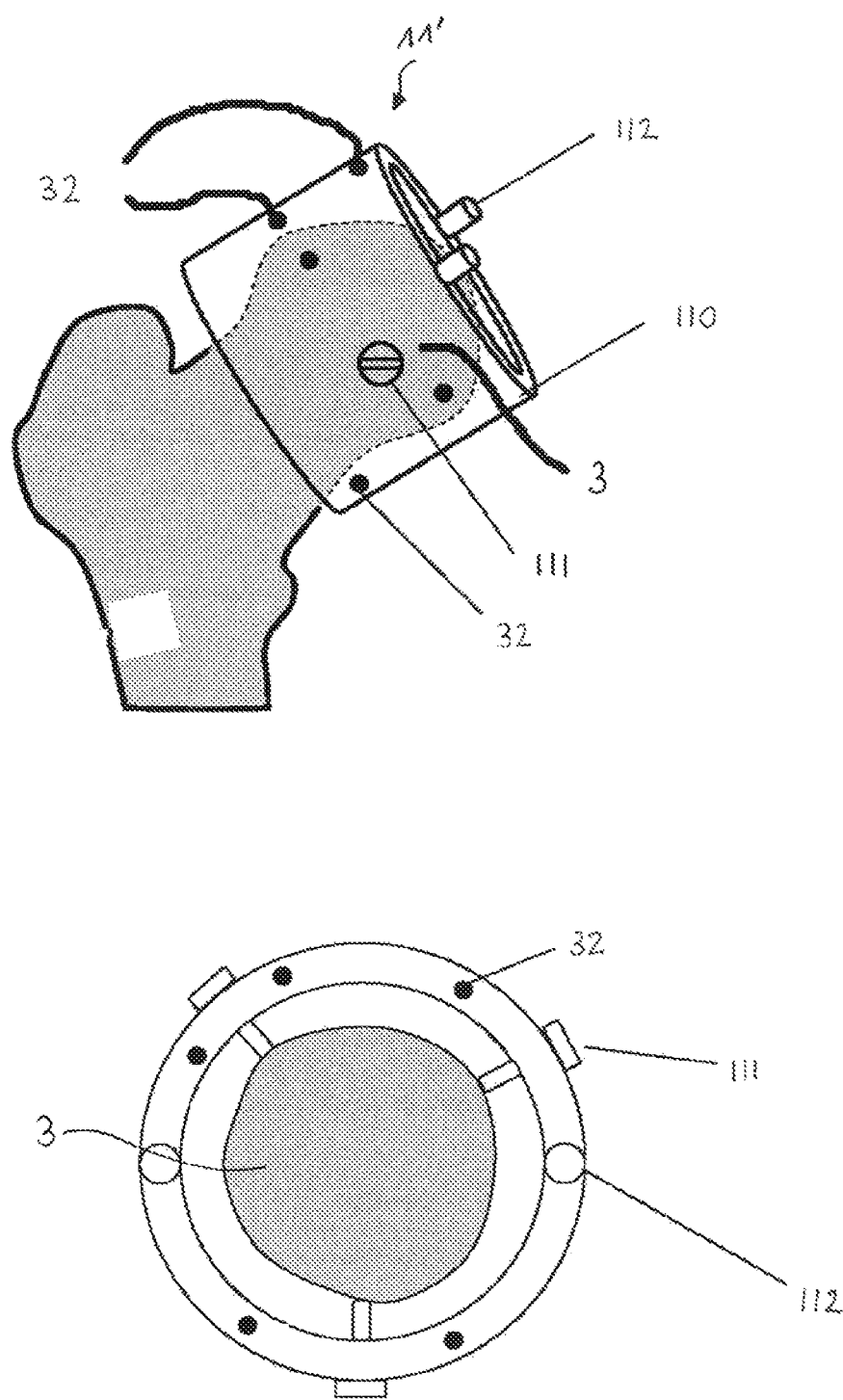
FIG. 17 shows another embodiment of a fixed part suited for hip surgery.

A further embodiment of the attachment unit 11' is shown in FIG. 17.

A collar 110 embraces a femoral head 3 and is locked with three screws 111.

Additionally the collar 110 comprises markers 32 for determination of the coordinates.

Using the attachments 112 the positioning unit can be connected to the attachment unit 11'.

EXAMPLE 3

Knee Surgery with a Navigation System

In another preferred embodiment, illustrated on FIGS. 7 and 8, the surgical application is the total replacement of the knee joint; the solid 3 is the patient's tibia or the basis of the instrument fixed to the tibia, and the tracker 30, rigidly fixed to the bone, allows the navigation system 2 to track the tibia; the instrument 1 is a cutting block on which a cutting plane 14 must be aligned with the desired target plane selected by the surgeon; the instrument mobile part position is adjustable by three screws; the position of the three screws determine a unique position of the cutting block with respect to the fixed part 11.

The cutting plane position is defined by a slope angle, a varus/valgus angle, and a cut thickness with respect to the tibia.

The target position is entered into the navigation system by the surgeon or set to default values with respect to anatomical landmarks digitized by the surgeon with the navigation system.

The goal of the device is then to adjust the position of the cutting block to the target position.

In one preferred embodiment, the surgical application is the total replacement of the knee joint; the solid 3 is the patient's femur or the basis of the instrument fixed to the femur, and the solid tracker 30, rigidly fixed to the bone, allows the navigation system 2 to track the femur; the instrument 1 is a cutting block on which a cutting plane 14 must be aligned with the desired target plane selected by the surgeon; the instrument mobile part position is adjustable by three screws 13; the position of the three screws determine a unique position of the cutting block with respect to the fixed part 11.

The plane position is defined by a slope angle, a varus/valgus angle, and a cut thickness with respect to the femur.

The target position is entered into the navigation system by the surgeon or set to default values with respect to anatomical landmarks digitized by the surgeon with the navigation system.

The goal of the device 4 is then to adjust the position of the cutting block in the target position.

EXAMPLE 4

Spacer Adjustment

In another preferred embodiment, not illustrated, the positioning unit is simply an adjustable spacer or distracter between two bones. A screw mechanism is used to move apart two parallel plates that generate a distance between two bones for ligament balancing check and optimization.

For example, one plate is positioned in contact with the tibia and the other one is positioned in contact with the femur, and the distance between the plates is adjusted by one screw.

Alternatively, 2 pairs of plates are located on the external and on the internal parts of the knee, thus being adjusted by two screws.

For adjusting quickly and precisely the spacer to a desired value, the actuated screwdriver is placed in the screw head and the number of turns is applied to obtain the desired distance.

It must be noted that the referencing method (navigation or medical imaging) is independent from the surgical instrument and application. Indeed, although knee surgery has been described with reference to a navigation system whereas hip resurfacing and spine surgery have been described with reference to an imaging system, the skilled person could practice knee surgery with an appropriate imaging system and hip resurfacing or spine surgery with a appropriate trackers of a navigation system.

REFERENCES

[1] Kosmopoulos V, Schizas C., Pedicle screw placement accuracy: a meta-analysis, Spine. 2007; 32(3): E111-20
[2] P. A. Grützner, A. Hebecker, H. Waelti, B. Vock, L.-P. Nolte, A. Wentzensen, Klinische Studie zur registrierungsfreien 3D-Navigation mit dem mobilen C-Bogen SIREMOBIL Iso-C 3D, Electromed. 2003; 71(1):58-67
[3] Schaeren S, Roth J, Dick W. Effective in vivo radiation dose with image reconstruction controlled pedicle instrumentation vs. CT based navigation, Orthopäde, 2002 April; 31(4):392-6
[4] P. Merloz, J. Tonetti, L. Pittet, M. Coulomb, S. Lavallee, J. Troccaz, P. Cinquin, P. Sautot, Computer assisted spine surgery: a clinical report, Comput Aided Surg. 1999; 3:297-305
[5] T. Laine, T. Lund, M. Ylikoski, J. Lohikoski, D. Schlenzka, Accuracy of pedicle screw insertion with and with-out computer assistance, European Spine Journal, 2000; 9(3): 235-240
[6] L. P. Amiot, K. Lang, M. Putzier, H. Zippel, H. Labelle, Comparative results between conventional and computer-assisted pedicle screw installation in the thoracic, lumbar, and sacral spine. Spine. 2000; 25:606-614
[7] Sukovich W, Brink-Danan S, Hardenbrook M. Miniature robotic guidance for pedicle screw placement in poste-rior spinal fusion: early clinical experience with the SpineAssist. Int J Med Robot. 2006 June; 2(2):114-22],
[8] P. A. Grützner, A. Hebecker, H. Waelti, B. Vock, L.-P. Nolte, A. Wentzensen, Klinische Studie zur registrierungsfreien 3D-Navigation mit dem mobilen C-Bogen SIREMOBIL Iso-C 3D. Electromed. 2003; 71(1):58-67;
[9] Wendl K, von Recum J, Wentzensen A, Grützner P A. Iso-C (3D-assisted) navigated implantation of pedicle screws in thoracic lumbar vertebrae. Unfallchirurg. 2003 November; 106(11):907-13
[10] Sukovich W, Brink-Danan S, Hardenbrook M. Miniature robotic guidance for pedicle screw placement in posterior spinal fusion: early clinical experience with the SpineAssist. Int J Med Robot. 2006 June; 2(2):114-22
[11] Hamadeh A, Lavallée S, Cinquin P. Automated 3-dimensional computed tomographic and fluoroscopic image registration. Comput Aided Surg. 1998; 3: 11-19
[12] Horn, B. K. P.: Closed-form solution of absolute orientation using unit quaternions. Journal of Optical Society of America A. (1987), Vol. 4, p. 629
[13] Susil, R. C.; Anderson, J. H.; Taylor, R. H.: A Single Image Registration Method for CT Guided Interventions. Medical Image Computing and Computer-Assisted Intervention. MICCAI'99. Springer (1999), p. 798-808

The invention claimed is:

1. A surgical system for alignment of a surgical guide with respect to a solid, said system comprising:
a positioning unit comprising a fixed part that is fixed with respect to the solid and a mobile part supporting the surgical guide, the position of said mobile part being adjustable with respect to the fixed part by screws, each screw having a head with a unique identification feature that distinguishes it from other screws of the positioning unit
a referencing unit for detecting a position of the positioning unit with respect to a target position of the surgical guide,
a control unit for computing a target position of each screw suitable for positioning the surgical guide in the target position, and
an adjustment device for adjusting the position of each screw, comprising:
a handle,
a stem comprising a tip suited to the head of the screw, the stem being coupled to the handle by a rolling system,
an actuated system for driving said stem in rotation with respect to the handle,
communication means to communicate with the control unit, wherein the control unit transmits to the actuated system the number of turns to apply to the stem to reach the target position of the screw, and
detection means for identifying which screw the tip of the stem is in contact with, wherein the detection means detects the unique identification feature upon contact of the tip of the stem with the head of the screw and identifies the contacted screw based on the respective identification feature, and
wherein the communication means of the device transmits identification information for said contacted screw from the detection means to the control unit.

2. The surgical system of claim 1, wherein the surgical guide comprises one or more drill guides or one or more cutting blocks.

3. The surgical system of claim 2, wherein the control unit is connected to an imaging system and the referencing unit comprises one or more calibration markers that are detectable by the imaging system.

4. The surgical system of claim 3, wherein the referencing unit is removably attached to an attachment unit rigidly fixed to the solid.

5. The surgical system of claim 2, wherein the control unit is included in a navigation system and the referencing unit comprises a first reference element attached to the solid or to the fixed part of the positioning unit, that generates a first three-dimensional reference tracker, which is independently registered in the navigation system and a second reference element applied to the mobile part of the positioning unit that needs to be adjusted, that generates a second three-dimensional reference tracker, which is independently registered in the navigation system.

6. The surgical system of claim 5, wherein the position of the mobile part of the positioning unit is adjusted to a target defined by use of the navigation system, and the control unit determines the number of turns to apply to each screw to reach the target.

7. The surgical system of claim 1, further comprising means for indicating to the user which screw should be turned and how many turns should be applied to each screw to reach the target.

8. The surgical system of claim 7, further comprising a ruler on the positioning unit, on the adjustment device or on both of the positioning unit and the adjustment device to adjust each screw.

9. The surgical system of claim 1, further comprising an attachment unit for attachment to the spine of a patient, the referencing unit being attached to the attachment unit and the positioning unit being attached to the attachment unit or to the referencing unit, the positioning unit comprising four screws for adjusting the position or orientation of a drill guide.

10. The surgical system of claim 1, further comprising an attachment unit for attachment to the femoral head of a patient, the referencing unit being attached to the attachment unit and the positioning unit being attached to the attachment unit or to the referencing unit, the positioning unit comprising four screws for adjusting the position or orientation of a drill guide.

11. The surgical system of claim 1, wherein the fixed part of the positioning unit is constructed for attachment to the tibia or to the femur of a patient, and the mobile part supports a cutting plane and three screws for adjusting the position of the cutting plane with respect to the fixed part.

12. The surgical system of claim 1, wherein the positioning unit is a spacer comprising two parallel plates and a screw for adjusting the distance between the plates.

13. The surgical system of claim 1, wherein said detection means comprises a sliding stem able to axially slide inside the stem, the sliding stem being constructed to be displaced with respect to the tip of the stem by contact of the tip with a head of a screw, and a position sensor adapted to measure axial displacement of the sliding stem with respect to the tip of the stem, the detection means being configured to identify the screw based on the measured axial displacement.

14. The surgical system of claim 1, wherein said detection means comprises first electrical connectors arranged at the tip of the stem and an ohmmeter connected to said first electrical connectors, each screw head having an electrical resistance, the ohmmeter being configured to measure said electrical resistance when the first electrical connectors at the tip of the stem contact the screw head, the detection means being configured to identify the screw based on the measured electrical resistance.

15. The surgical system of claim 1, wherein the detection means comprises a "Hall effect" sensor arranged in the tip of the stem, each screw head having a magnet at a corresponding buried depth, the Hall effect sensor being configured to detect the corresponding buried depth of the respective magnet when the tip of the stem contacts the screw head, the detection means being configured to identify the screw based on the detected buried depth.

16. The surgical system of claim 1, wherein said detection means comprises an optical sensor, a first optical fiber and a second optical fiber, the first and second optical fibers being arranged inside the stem so as to respectively light a cavity of a screw head and bring reflected light to said optical sensor, the detection means being configured to identify the screw based on the reflected light from the screw head cavity.

17. The surgical system of claim 1, wherein the control unit is configured to transmit to the actuated system the number of turns to apply to the stem for the contacted screw after receiving the identification information for said contacted screw from the detection means.

18. A surgical system for alignment of a surgical guide with respect to a solid, said system comprising:
    a positioning unit comprising a fixed part that is fixed with respect to the solid and a mobile part supporting the surgical guide, the position of said mobile part being adjustable with respect to the fixed part by screws,
    a referencing unit for detecting a position of the positioning unit with respect to a target position of the surgical guide,
    a control unit for computing a target position of each screw suitable for positioning the surgical guide in the target position, and
    an adjustment device for adjusting the position of each screw, comprising:
        a handle,
        a stem comprising a tip suited to the head of the screw, the stem being coupled to the handle by a rolling system,
        an actuated system for driving said stem in rotation with respect to the handle,
        communication means to communicate with the control unit, wherein the control unit transmits to the actuated system the number of turns to apply to the stem to reach the target position of the screw, and
        a tracker rigidly attached to the handle of the device, and
    wherein the control unit is configured to determine which screw the tip of the adjustment device is in contact with based at least on detection of a position of said tracker by the referencing unit.

* * * * *